United States Patent
Becker et al.

(10) Patent No.: US 6,916,928 B2
(45) Date of Patent: Jul. 12, 2005

(54) FUNCTIONALIZED PERYLENE TETRACARBOXYLIC ACID DIIMIDES

(75) Inventors: Stefan Becker, Mannheim (DE); Harm-Anton Klok, Mainz (DE); Juan Rodriguez-Hernandez, Mainz (DE); Falk Schuch, Wiesbaden (DE); Klaus Müllen, Cologne (DE)

(73) Assignee: Max-Planck-Gesellschaft der Wissenschaftene.V., Munich (DE)

( * ) Notice: Subject to any disclaimer, the term of this patent is extended or adjusted under 35 U.S.C. 154(b) by 0 days.

(21) Appl. No.: 10/343,750

(22) PCT Filed: Aug. 11, 2001

(86) PCT No.: PCT/EP01/09319

§ 371 (c)(1),
(2), (4) Date: Feb. 6, 2003

(87) PCT Pub. No.: WO02/14414

PCT Pub. Date: Feb. 21, 2002

(65) Prior Publication Data

US 2004/0024151 A1 Feb. 5, 2004

(30) Foreign Application Priority Data

Aug. 14, 2000 (DE) .......................... 100 39 643

(51) Int. Cl.⁷ .......................... C07D 471/02; C08F 2/00; C09K 11/06
(52) U.S. Cl. .................... 546/37; 526/204; 252/301.16; 252/700
(58) Field of Search ...................... 546/37; 252/174.23, 252/301.16, 700; 526/204

(56) References Cited

U.S. PATENT DOCUMENTS

| | | |
|---|---|---|
| 4,845,223 A | 7/1989 | Seybold et al. |
| 5,122,306 A | 6/1992 | Van Moer et al. |
| 5,281,367 A | 1/1994 | Schleck et al. |
| 5,597,517 A | 1/1997 | Chopdekar et al. |
| 5,705,103 A | 1/1998 | Chopdekar et al. |
| 6,063,181 A | 5/2000 | Böhm et al. |
| 6,184,378 B1 | 2/2001 | Böhm et al. |

FOREIGN PATENT DOCUMENTS

| | | |
|---|---|---|
| FR | 2 770 222 | 4/1999 |
| WO | 97/22607 | 6/1997 |
| WO | 99 40123 | 8/1999 |

OTHER PUBLICATIONS

Database Chemabs 'Online! 2001 Database accession no. 135:92965 XP002192518.

Y. Nagao Prog. Org. Coat., vol. 31, No. 1–2, pp. 43–49 1997.

K. Muellen et al. Polymer Materials Encyclopedia, vol. 7, pp. 4999–5009 1996.

W. Herbst et al. Industrial Organic Pigments—Production, Properties, Applications, vol. 2, pp. 478–479 1997.

G. Seybold et al. Dyes Pigm., vol. 11, pp. 303–317 1989.

R. Reisfeld et al. Chimia, vol. 44, pp. 295–297 1990.

H.G. Loehmannsroeben et al. Appl. Phys., vol. B48, pp. 449–452 1989.

S. Haremza Chem. in Unserer Zeit, vol. 28, p. 233 1994.

*Primary Examiner*—Charanjit S. Aulakh
(74) *Attorney, Agent, or Firm*—Oblon, Spivak, McClelland, Maier & Neustadt, P.C.

(57) ABSTRACT

The present invention relates to the use of functionalized perylene-3,4,9,10-tetracarboxylic acid diimides as initiator and/or co-reactant for polymerization reactions, to polymers prepared using the perylene-3,4,9,10-tetracarboxylic acid diimide compounds, to the use of these colored and/or fluorescent polymers, and to novel functionalized perylene-tetracarboxylic acid diimides.

31 Claims, 8 Drawing Sheets

FUNCTIONALIZED PERYLENE TETRACARBOXYLIC ACID DIIMIDES

The present invention relates to the use of functionalized perylene-3,4,9,10-tetracarboxylic acid diimides as initiator and/or co-reactant for polymerization reactions, to polymers prepared using the perylene-3,4,9,10-tetracarboxylic acid diimide compounds, to the use of these colored and/or fluorescent polymers, and to novel functionalized perylenetetracarboxylic acid diimides.

Diimides of 3,4,9,10-perylenetetracarboxylic acid are dyes which are distinguished by high tinting strength, good solvent resistance, good resistance to chemicals and excellent thermal stability. These dyes or pigments furthermore have high hiding power and excellent light and weathering stability (Y. Nagao, Prog. Org. Coat. 31 (1–2) (1997), 43; K. Müllen et al., Polymer Materials Encyclopedia (Editor J. C. Salamone) Vol. 7, CRC Press Inc., (1996), 4999).

Perylene derivatives are therefore used as high-performance dyes/pigments for coloring engineering plastics, in high-quality spray paints or as emulsion paints (W. Herbst et al., Industrial Organic Pigments—Production, Properties, Applications, 2nd Edition, Wiley—VCH, Weinheim (1997)). Since, in particular, soluble perylenetetracarboxylic acid diimides frequently exhibit strong fluorescence with quantum yields of up to virtually 100%, they are furthermore employed as functional dyes, for example in fluorescent solar collectors (G. Seybold et al., Dyes Pigm., 11 (1989), 303; M. J. Cook et al., Chem. Ber., 20 (1984), 914), as laser dyes (R. Reisfeld et al., Chimia 44 (1990), 295; H. G. Löhmannsröben et al., Appl. Phys. B48 (1989), 449) or in greenhouse sheeting (JP 62-132693; S. Haremsa, Chem. in unserer Zeit, 28 (1994), 233).

Perylenetetracarboxylic acid diimide compounds have been used, for example, for the preparation of chemoluminescent compositions (U.S. Pat. Nos. 5,705,103; 5,597,517; 5,281,367; 5,122,306). Compositions of this type are obtained by mixing an oxalate, an activator and a perylene derivative.

U.S. Pat. No. 4,845,223 describes perylenetetracarboxylic acid diimide derivatives which are used as fluorescent dyes. These dyes are admixed with the material to be colored, for example a polymethyl methacrylate. WO 97/22607 describes 1,7-disubstituted perylene-3,4,9,10-tetracarboxylic acid diimides as intermediates in the preparation of the corresponding dianhydrides. WO 99/40123 relates to aqueous polymer dispersions which comprise dyes, including perylene dyes. The use of 2,9-dibutyl-5,6,12,13-tetra[4-hydroxymethylphenoxy]-3,4,9,10-perylenetetracarboxlic acid diimide for the preparation of an electroluminescent diode material is disclosed in FR 2770222.

It is an object of the present invention to provide improved perylene-3,4,9,10-tetracarboxylic acid diimide compounds and to develop new fields of application for these dyes.

We have found that this object is achieved by the use of perylene-3,4,9,10-tetracarboxylic acid diimide compounds of the formula (I)

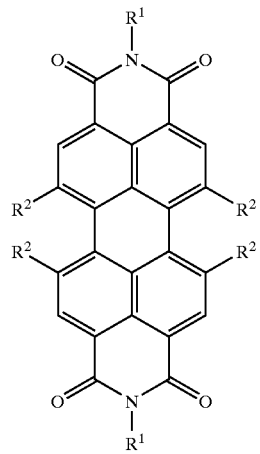

in which each $R^1$ is, independently of the others, an alkyl or aryl group, which may be unbranched or branched and/or unsubstituted or substituted, and each $R^2$ is, independently of the others, H, halogen, $C_1$–$C_4$-alkyl, $C_1$–$C_4$-alkoxy or a radical which contains at least one functional group Y selected from hydroxyl, ether, ester, halogen, amine, amide, thiol, an ethylenically unsaturated double bond, an acetylenically unsaturated triple bond and/or carboxyl, which may, if desired, be provided with a protecting group or an activating group, with the proviso that at least one $R^2$ contains a functional group Y, as initiator and/or co-reactant for a polymerization reaction.

It has been found that perylenetetracarboxylic acid diimides which have been functionalized in accordance with the invention can be employed as initiator for various polymerization reactions or as co-reactants in polymer-analogous reactions. A common feature of all the perylene-3,4,9,10-tetracarboxylic acid diimide compounds which are suitable for the use proposed here is that they have at least one radical containing a functional group in positions 1, 6, 7 and/or 12, with the functional group forming a covalent bond in a polymerization reaction. Functional groups of this type can exist in free form, for example as —OH, —NH$_2$, —SH, halogen, in particular Br, as an olefinic double bond (C=C), as a triple bond (C≡C) or as —COOH. However, the functional group Y can also be in activated form, for example as the acid amide, or protected, for example as an ester, amide, carbamate or ether. Suitable activating groups for Y=COOH are active esters, such as N-hydroxysuccinimidyl ester (NHS ester), N-hydroxybenzotriazolyl ester (HOBt ester), pentafluorophenyl ester (OPfp ester) and p-nitrophenyl ester. Suitable activating groups for Y=OH are sulfonic acid esters (for example tosylate, mesylate and triflate), carbonates (for example benzotriazolylcarbonate [BTC], p-nitrophenylcarbonate [NPC]), glycidyl ethers (epoxides) and carbonylimidazole (CDI).

Owing to the thermal, chemical and photochemical stability of perylenetetracarboxylic acid diimide compounds, these chromophores are able to withstand various polymerization reaction conditions without losing their dye character. Thus, it has been observed that the perylene compounds employed in accordance with the invention remain stable under reaction conditions as occur, for example, in a free-radical polymerization, in a ring-opening polymerization of aliphatic polyesters, cyclic siloxanes or N-carboxyanhydrides and even at high temperatures of polycondensation reactions. It is therefore possible to add the perylene compounds as initiator or co-reactant even before or during the polymerization reaction and not to admix them with the finished polymer until a later time. The addition as initiator or co-reactant has the effect that the perylene compounds employed in accordance with the invention are covalently bonded into the polymers formed. This covalent bonding prevents undesired migration or aggregation of the dyes, as can occur on simple admixing of dyes with polymers, in the plastic matrix.

The polymer chains covalently bonded to the dye additionally have an advantageous action here as compatibilizer with the matrix, i.e. they make the dye compatible with the matrix in order thus to prevent separation phenomena. In addition, the polymer chains covalently bonded to the dye effectively screen the chromophore. This property is particularly advantageous for optical and opto-electronic applications of polymers since the fluorescence quantum yield is kept at a high level by this screening and any undesired color change due to aggregation is prevented.

The term initiator, as used herein, denotes a molecule which is able to initiate a polymerization reaction.

The term co-reactant for a polymerization reaction denotes a molecule which is reacted and covalently bonded in a polymerization reaction and thus contributes to the growth of the polymer chains.

The term polymerization reaction covers all reactions which include chain growth. Examples of polymerization reactions are free-radical polymerization reactions, polyadditions, polycondensations, anionic polymerizations, cationic polymerizations and coordinative polymerizations. In a polymerization reaction, a low-molecular-weight compound, for example a monomer or oligomer, is generally converted into a high-molecular-weight compound, for example a polymer.

On use as initiator, the functionalized dyes can serve as starters for grafting from polymerization reactions. Examples of polymerization reactions of this type using a functionalized perylene dye are the synthesis of polyesters, for example polycaprolactones, polylactides or polyamides, in particular nylon, or polypeptides, for example by polymerization of amino acid N-carboxyanhydrides, of polysiloxanes, of polystyrenes or poly(meth)acrylates. On use of perylene compounds containing two functional groups Y, linear polymers are accessible in this way, while on use of perylene dyes containing three or more functional groups Y, star polymers are obtained.

In a further preferred embodiment, the functionalized perylene dyes are used in grafting-onto reactions, in which suitably functionalized polymer chains, for example polyalkylene oxides, in particular polyethylene glycol, polystyrenes or polypeptides, are covalently bonded to the perylene dyes.

The functionalized perylene dyes can also be copolymerized as co-reactants, in particular as comonomers, with other monomers in order to form a polymeric dye or a colored polymer. In this way, for example, colored polyurethanes, polyparaphenylenes, polyfluorenes or polystilbenes can be prepared. On use of perylene compounds having three or more functional groups Y, these may additionally act as crosslinking agents.

The functionalized perylene dyes may furthermore also be used as reactive dyes for coloring polymers, in particular engineering polymers. To this end, the functionalized dyes are subjected to a polymer-analogous reaction, for example a transesterification, together with suitable monomers and, if desired, auxiliaries, with the functionalized perylene dyes being covalently bonded into the polymer skeleton. The dyes here can be covalently bonded both into the main polymer chain and into or as a side chain. It is particularly advantageous to carry out the reaction in an extruder. If functionalized perylene derivatives having three or more functional groups Y are employed, they can additionally take on the function of a crosslinking agent here.

The perylene tetracarboxylic acid diimide fluorophores preferably have long-wave, red fluorescence which is favorable for many applications, in particular bioscientific applications. The functionalized perylene dyes employed in accordance with the invention preferably have fluorescence at a wavelength >500 nm and particularly preferably at a wavelength >550 nm.

The dyes employed in accordance with the invention have at least one radical $R^2$ which contains a functional group Y which enables covalent bonding of the dyes into polymer molecules. The other radicals $R^2$ are selected from units which are inert under the polymerization reaction conditions, for example H, halogen, in particular Br or Cl, $C_1$–$C_4$-alkyl, $C_1$–$C_4$-alkoxy, $C_5$–$C_{15}$-aryl and $C_5$–$C_{15}$-aryloxy, in particular phenoxy. The aryl radicals or aryloxy radicals may themselves be substituted by an inert radical, for example $C_1$–$C_4$-alkyl. The radicals $R^2$ containing at least one functional group Y can basically be any desired organic radicals. They are preferably an alkyl or aryl radical which can be unbranched or branched and is substituted by at least one functional group Y and, if desired, by further substituents. Suitable radicals which can be substituted by a functional group Y are, for example, $C_1$–$C_{30}$-alkyl radicals, $C_1$–$C_{30}$-alkoxy radicals, $C_1$–$C_{30}$-alkylthio radicals, $C_5$–$C_{30}$-aryl radicals and preferably $C_5$–$C_{30}$-aryloxy or -arylthio radicals. In addition to the functional group Y, the radicals $R^2$ may have further inert substituents, for example $C_1$–$C_{30}$-alkyl radicals. The functional group Y is preferably —OH, —OR (where R is a $C_1$–$C_{30}$-hydrocarbon radical or a silyl radical, which may be unsubstituted or substituted, in particular an unsubstituted or substituted methyl, benzyl, or ethyl radical or a substituted silyl radical), $O(C{=}O)(CH_2)_n$Hal, $NH_2$, NHBoc, NHCBZ, $NH(C{=}O)(CH_2)_n$Hal, $O(C{=}O)(CH_2)_nCH_3$ or COOH (in which n is a number from 1 to 30, preferably from 1 to 8).

At least one radical $R^2$ particularly preferably has the structure

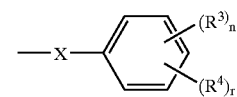

where X is O or S, n is an integer from 1 to 5, r is an integer from 0 to 5, with the proviso that n+r≦5, each $R^3$, independently of the others, is an alkyl or aryl group, which may be unbranched or branched, unsubstituted or substituted, and has at least one functional group Y as substituent, and $R^4$ is $C_1$–$C_4$-alkyl. Examples of particularly preferred radicals $R^2$ are

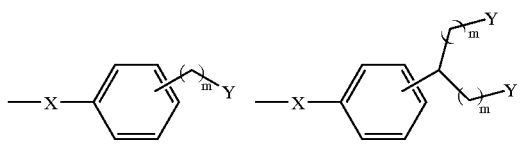

where X and Y are as defined above, and m is on each occurrence, independently of the others, an integer from 1 to 30, preferably from 1 to 8 and particularly preferably 1 or 2.

For the purposes of the invention, particular preference is given to perylene derivatives which contain at least two functional groups Y or at least four functional groups Y. Compounds containing two functional groups Y can be employed, for example, as initiator for the preparation of linear polymers or as comonomer for chain extension. Compounds containing four functional groups Y can be employed, for example, for the preparation of star-shaped polymers having four arms or as crosslinking agents.

Each radical $R^1$ bonded to the nitrogen atom of the carboximide group is, independently of the others, an alkyl or aryl group which may be unbranched or branched, unsubstituted or substituted. The radical $R^1$ is preferably a $C_1$–$C_{30}$-, in particular a $C_1$–$C_8$- and particularly preferably a $C_1$–$C_4$-alkyl group. It has been found that compounds in which at least one radical $R^1$ comprises an aromatic group, for example a $C_5$–$C_{30}$-aryl group, in particular a $C_5$–$C_{10}$-aryl group, which may, if desired, also contain heteroatoms, for example N, O or S, have particularly high stability. Suitable substituents for $R^1$ are, for example, inert substituents, for example hydrocarbon radicals having from 1 to 30 carbon atoms, in particular $C_1$–$C_4$-alkyl, or functional groups, in particular the group Y defined above. While the radical $R^1$ can be selected in such a way that it is inert under the polymerization reaction conditions, i.e. does not participate in the polymerization reaction, it is advantageous for many applications for at least one radical $R^1$ also to contain one or more functional groups Y. In this way, the functionality of the functional dyes can be increased further. Through a suitable choice of substituents in which, for example, the radicals $R^2$ contain four functional groups Y and the radicals $R^1$ contain two further functional groups, it is thus possible, for example, to obtain a hexafunctionalized dye.

$R^1$ is preferably a phenyl radical of the formula

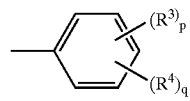

where $R^4$ is $C_1$–$C_4$-alkyl, i.e. in particular methyl, ethyl, propyl, isopropyl, butyl, isobutyl or tert-butyl, $R^3$ is as defined above, and p and q are each an integer from 0 to 5, with the proviso that p+q≦5.

Examples of particularly preferred radicals $R^1$ are

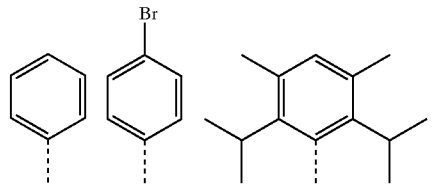

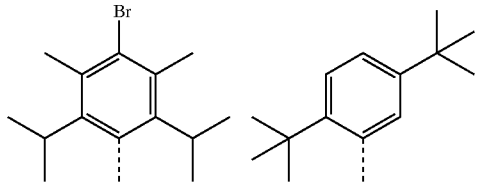

In the case where the radical $R^1$ contains one functional group, it preferably has the formula

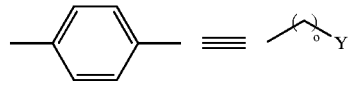

where o is an integer from 1 to 30, preferably from 1 to 8 and particularly preferably 1 or 2.

The invention furthermore relates to colored and/or fluorescent polymers which can be obtained using a perylene compound as initiator and/or co-reactant for a polymerization reaction, as described above. The colored and/or fluorescent polymers according to the invention contain a covalently bonded perylene chromophore and are formed from the functionalized perylene compounds described above and at least one monomer. Examples of suitable monomers are compounds containing a polymerizable group which can be reacted with the functional group Y. Particular preference is given to styrene, acrylic acid, acrylates and acrylamides, methacrylic acid, methacrylates and methacrylamides, oxazolines, cyclic olefins (for example norbornene), α,ω-diolefins, organosilicon compounds (in particular cyclosiloxanes), amino acids (particularly in the form of the N-carboxyanhydrides), peptides, ethers, in particular cyclic ethers, for example ethylene oxide, esters, caprolactones, lactides, etc. Since the dye is covalently bonded into the polymers according to the invention, separation, aggregation or migration of the dye within the plastic matrix cannot occur, and polymers having constant and uniform color properties are obtained.

Attachment of water-soluble polymer chains, for example of polypeptides or polyalkylene oxides, in particular polyethylene oxide, to the functionalized perylenetetracarboxylic acid diimides also enables water-soluble fluorescent substances to be obtained. These water-soluble fluorescent substances are, surprisingly, also fluorescent in aqueous solution or in water, while unfunctionalized perylenetetracarboxylic acid diimides are usually neither soluble nor fluorescent in water. Particularly preferred examples of such substances are star-shaped polypeptides, which exhibit strong fluorescence even in aqueous solution.

Fluorescence labeling with the polymers according to the invention additionally brings the advantage of ready detectability, since fluorescence can be measured sensitively, down to the fluorescence of a single molecule. This opens up particularly effective applications in the biosciences. Perylenetetracarboxylic acid diimides which are covalently bonded, for example, to polypeptide, polylactide or polycaprolactone chains can be used, for example, as fluorescent labels for drug-delivery or drug-release systems, whose behavior can then readily be observed from the fluorescence in in-vitro or in-vivo tests. The use of perylenetetracarboxylic acid diimide chromophores which have long-wave, red fluorescence, in particular at an emission wavelength >500 nm, is particularly advantageous here. Virtually no interfering background fluorescence is observed in biological samples in this spectral region.

The invention furthermore relates to the functionalized perylenetetracarboxylic acid diimide compounds presented above which contain at least one group which facilitates covalent bonding thereof to monomers or polymers. In particular, the invention also relates to perylene-3,4,9,10-tetracarboxylic acid diimide compounds of the formula (I)

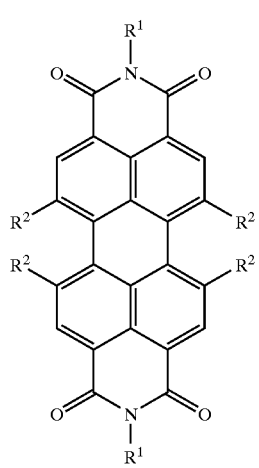

(I)

in which each $R^1$ is, independently of the others, an aryl radical, which may be unsubstituted or substituted, and each $R^2$ is, independently of the others, H, halogen, $C_1$–$C_4$-alkyl, $C_1$–$C_4$-alkoxy, $C_5$–$C_{15}$-aryl, $C_5$–$C_{15}$-aryloxy or a radical which contains at least one functional group Y selected from hydroxyl, ether, ester, amine, amide, thiol, an ethylenically unsaturated double bond, an acetylenically unsaturated triple bond and/or carboxyl, which may, if desired, be provided with a protecting group or an activating group, with the proviso that the radicals $R^2$ contain a total of three or more functional groups Y.

Preferred embodiments of the radicals $R^1$ and $R^2$ are as described above.

Preference is furthermore given to perylene-3,4,9,10-tetracarboxylic acid diimide compounds of the formula (I) in which one or both radicals $R^1$ contain at least one Br substituent, and each $R^2$ is, independently of the others, H, halogen, $C_1$–$C_4$-alkyl, $C_1$–$C_4$-alkoxy, $C_5$–$C_{15}$-aryl, $C_5$–$C_{15}$-aryloxy or a radical which contains at least one functional group Y selected from hydroxyl, ether, ester, halogen, amine, amide, thiol, an ethylenically unsaturated double bond, an acetylenically unsaturated triple bond and/or carboxyl, which may, if desired, be provided with a protecting group or an activating group, with the proviso that at least one $R^2$ contains a functional group Y. Compounds of this type are suitable, in particular, as intermediates for the preparation of polyfunctionalized perylene compounds, which can then be covalently bonded into polymer chains in the manner described above.

The functionalized perylene-3,4,9,10-tetracarboxylic acid diimide compounds described above can be obtained by reactions known to the person skilled in the art.

The invention is explained in greater detail by the attached figures and the following examples.

EXAMPLES

Figure 1:
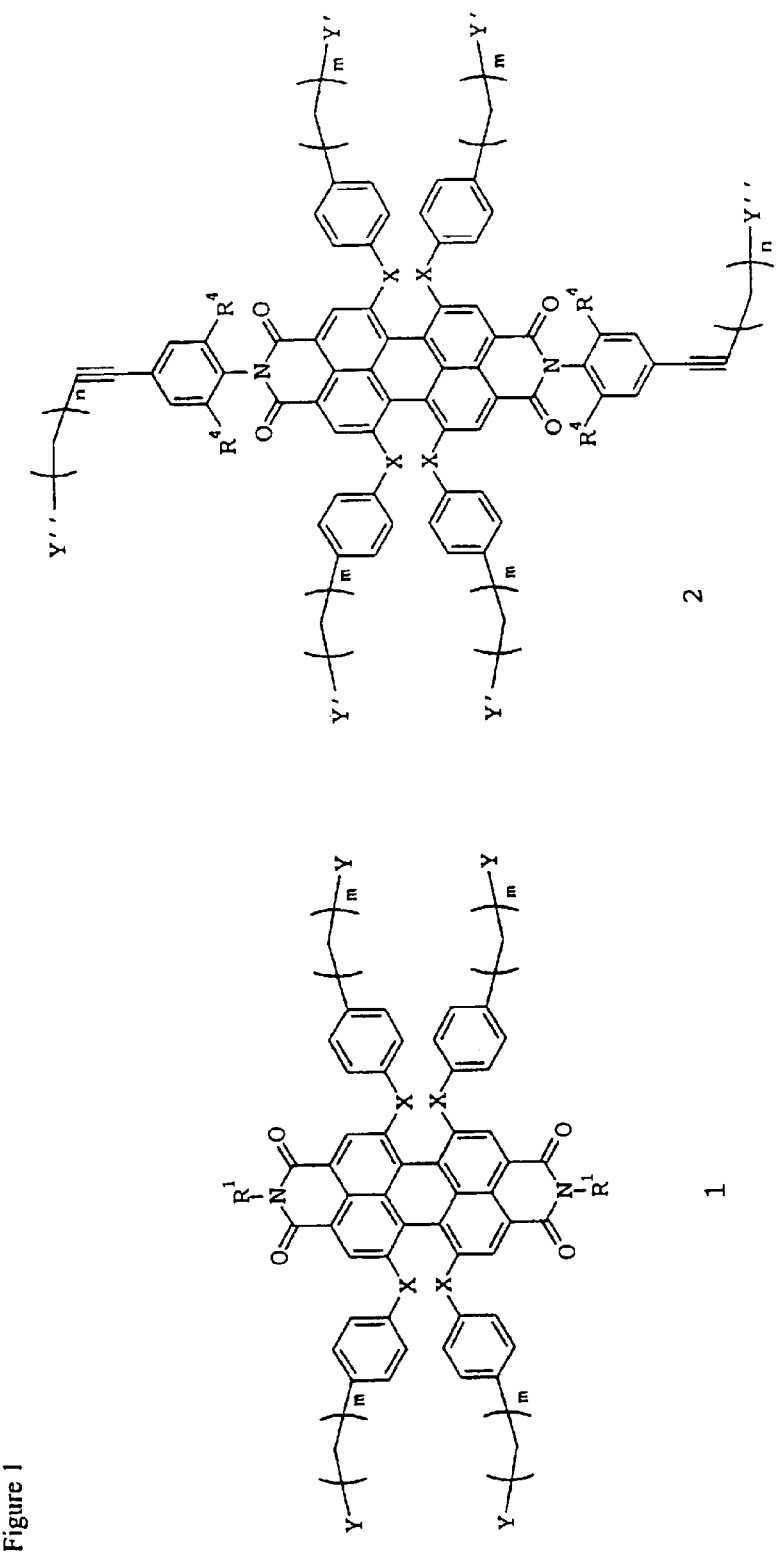
FIG. 1 shows preferred structures of the functionalized perylenetetracarboxylic acid diimides according to the invention.
Figure 1:
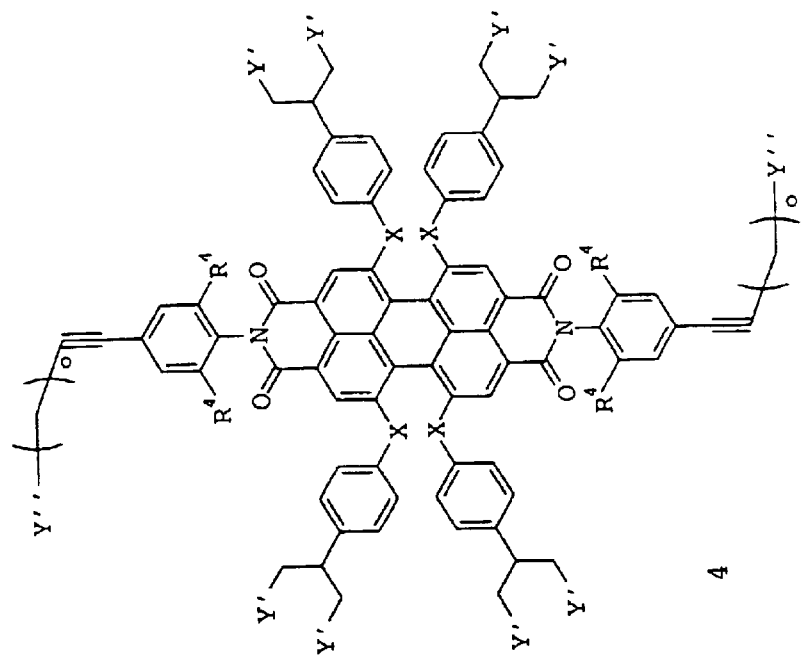
Figure 1:
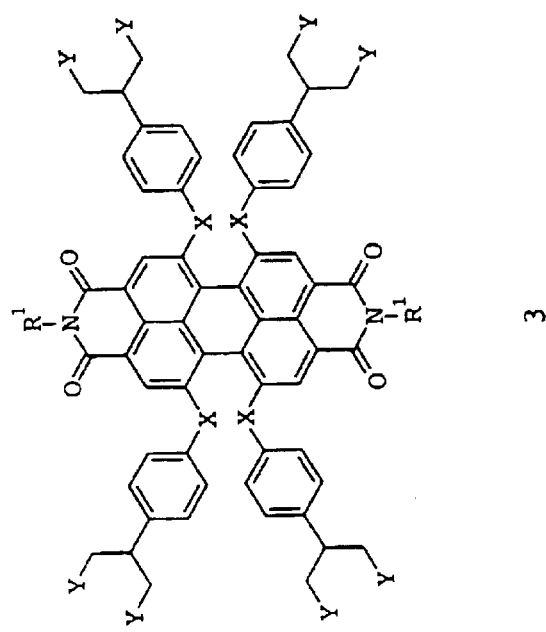
Figure 1:
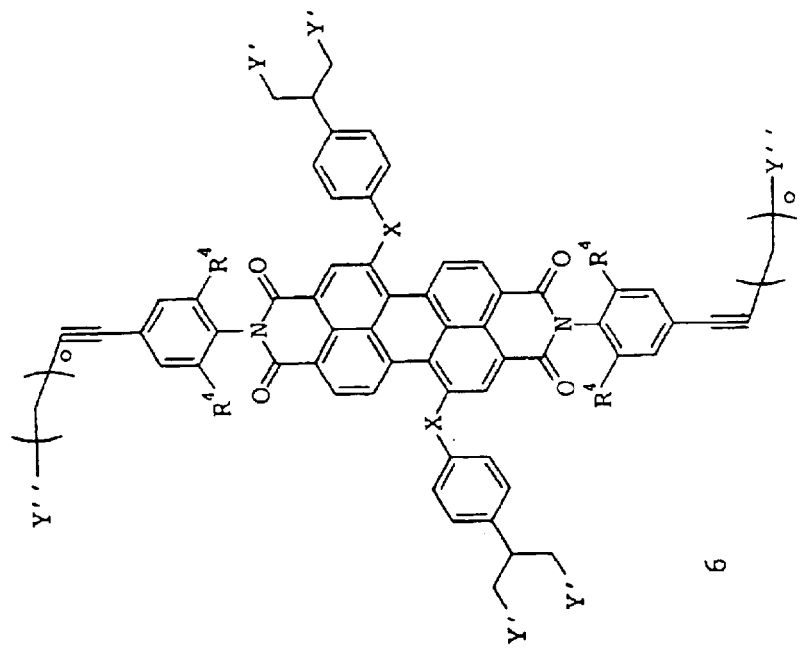
Figure 1:
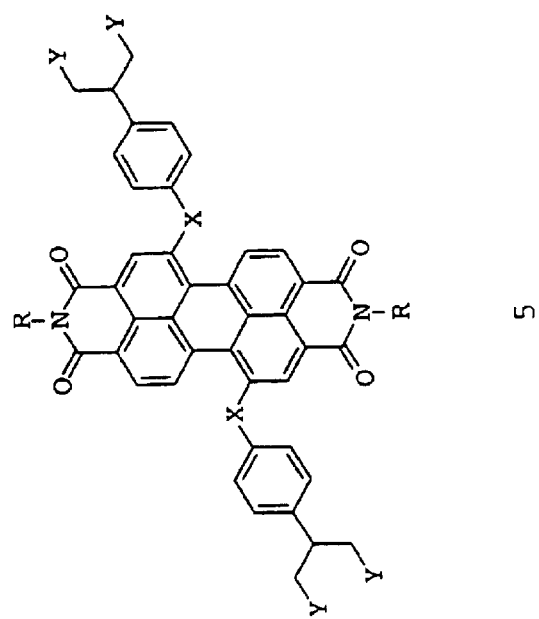
Figure 1:
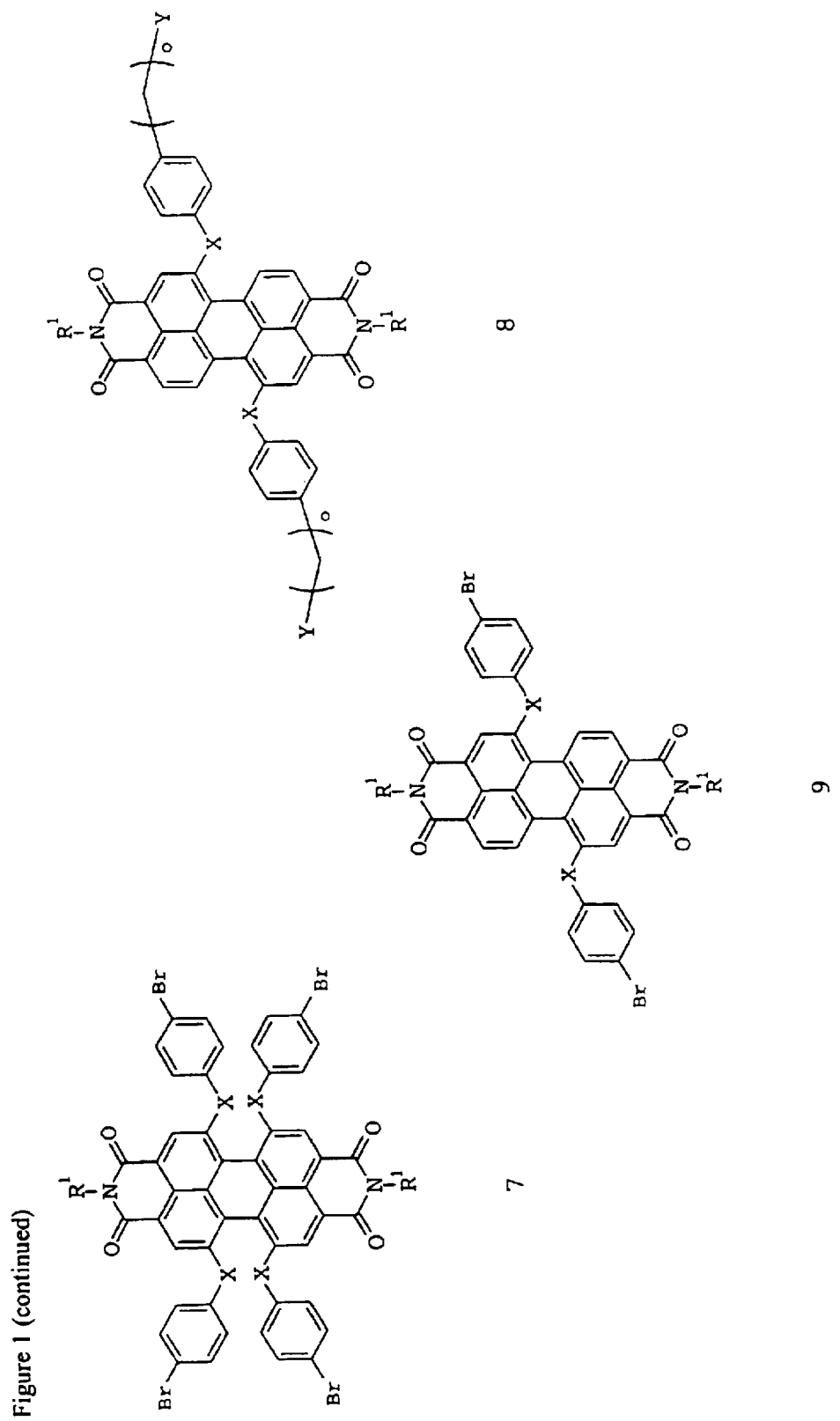
Figure 2:
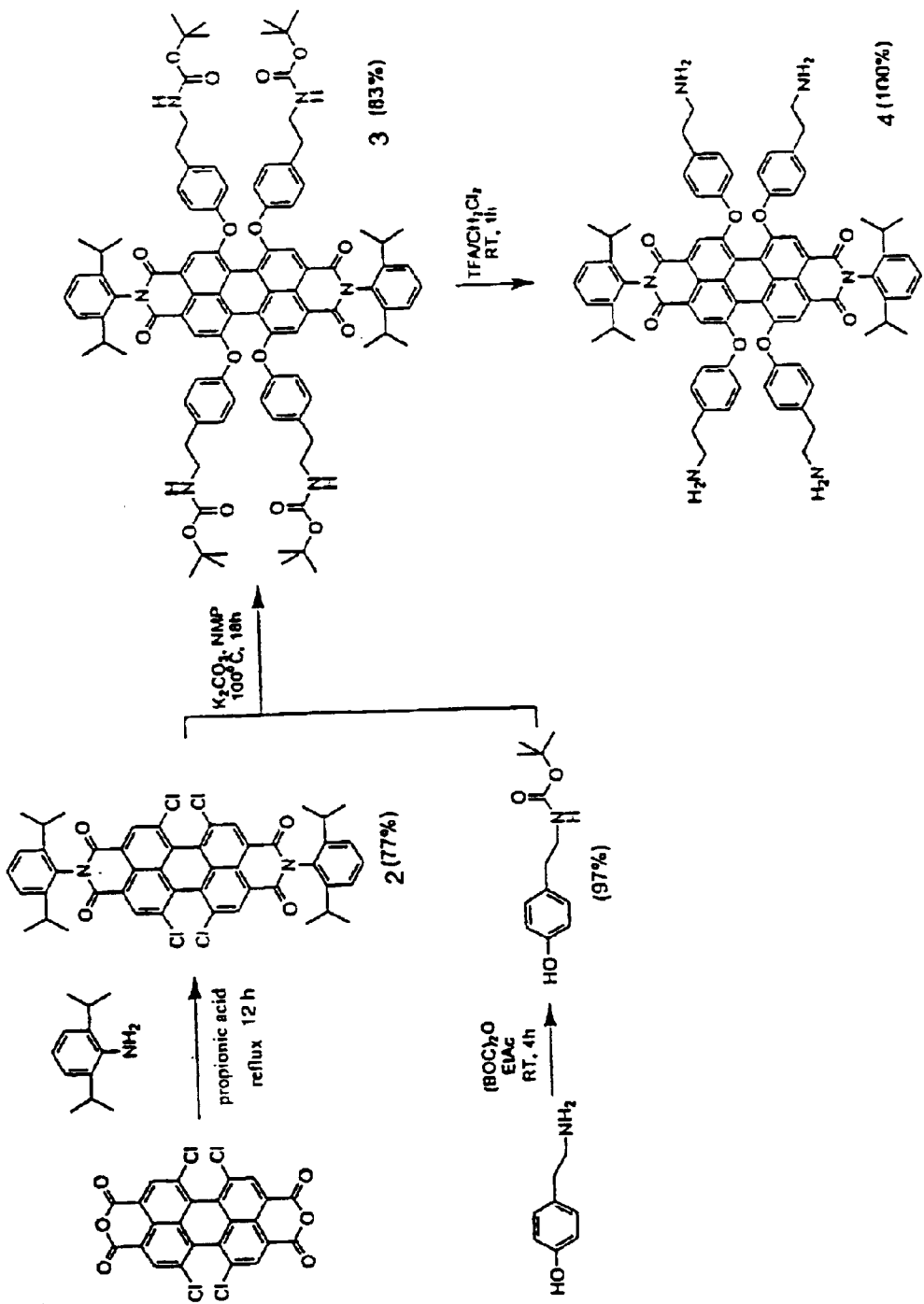
FIG. 2 shows a synthetic route for the preparation of a perylenetetracarboxylic acid diimide which is tetrafunctionalized by primary amino groups.
Figure 3:
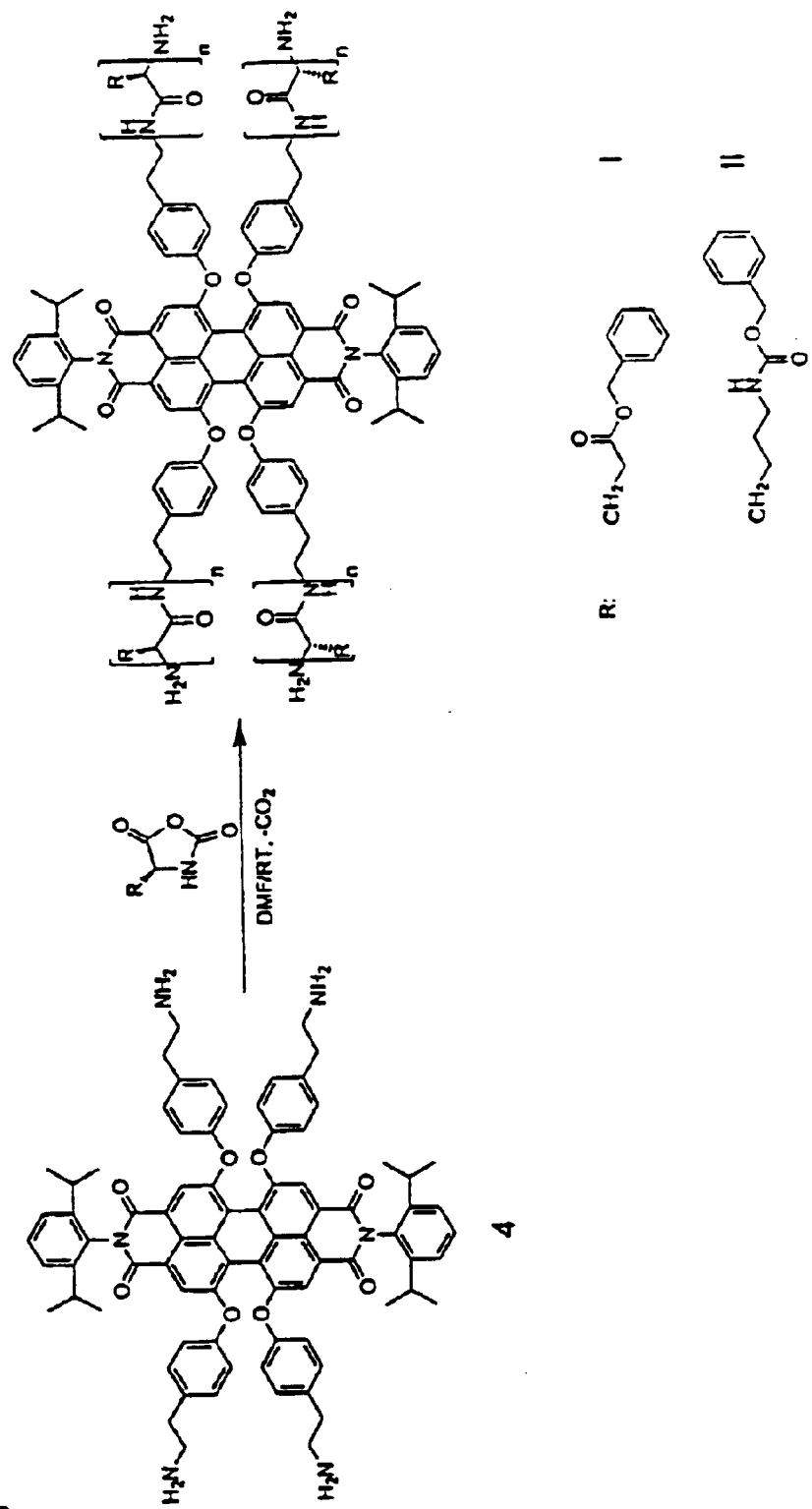
FIG. 3 shows a synthetic route for the preparation of a star-shaped polypeptide which is provided with protecting groups.
Figure 4:
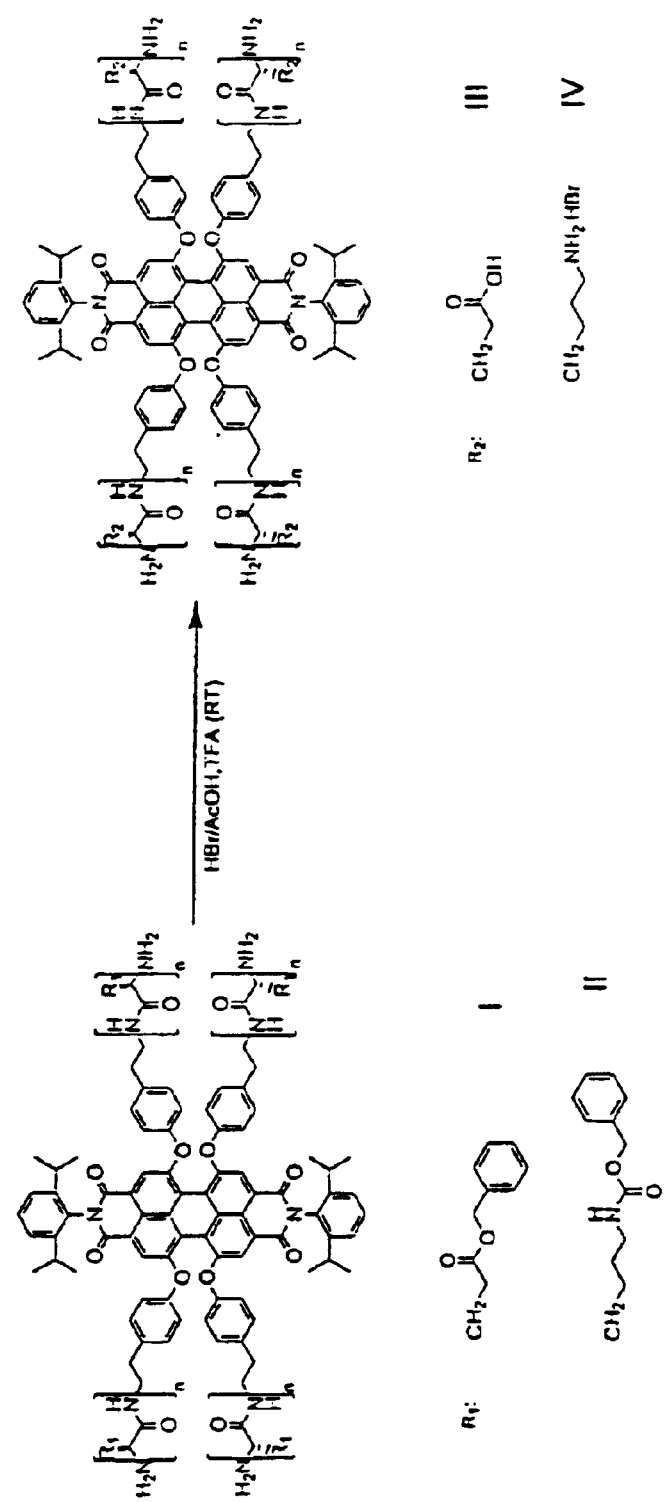
FIG. 4 shows the formation of a water-soluble, star-shaped polypeptide which is even fluorescent in aqueous solution.
Figure 5:
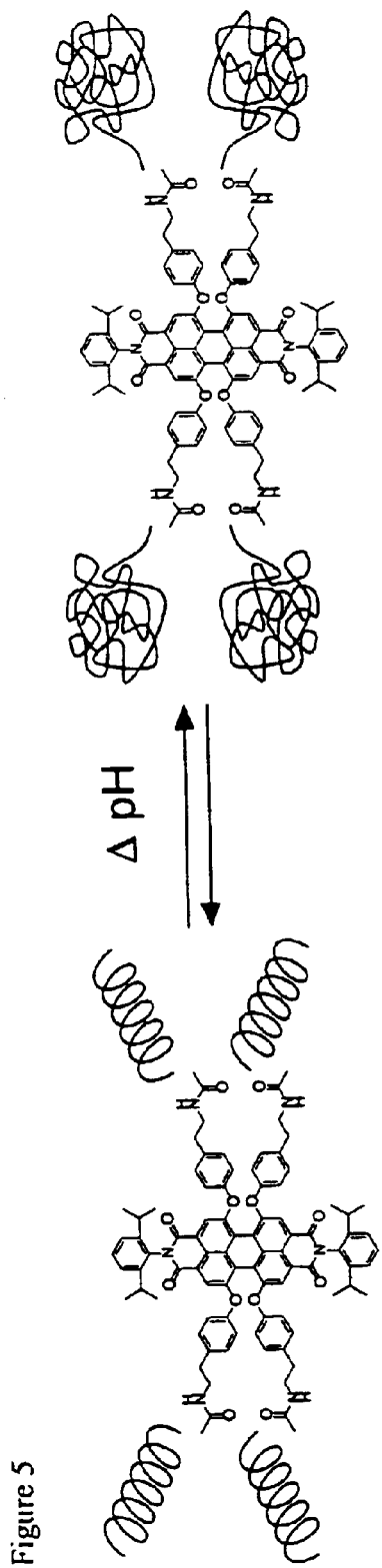
FIG. 5 shows the pH dependence of the conformation of polypeptide chains on the dye initiator.

| Abbreviations used: | |
|---|---|
| arom. CH (NMR spectrum) | aromatic ternary C atom |
| aq | aqueous |
| arom. Q (NMR spectrum) | aromatic quaternary C atom |
| calc. | calculated |
| conc. | concentrated |
| δ | chemical shift [ppm] |
| d (NMR spectrum) | doublet |
| DMF | dimethylformamide |
| DP | degree of polymerization |
| DSC | differential scanning calorimetry |
| FD (mass spectrum) | field desorption |
| GPC | gel permeation chromatography |
| h | hours |
| h (NMR spectrum) | heptet |
| λ | wavelength |
| m (NMR spectrum) | multiplet |
| M | molecular weight [g/mol] |
| $M_n$ | number average |
| $M_w$ | weight average |
| NMP | N-methyl-2-pyrrolidone |
| NMR | nuclear magnetic resonance |
| ν | wavenumber |
| PACL | poly(tert-amylcaprolactone) |
| PCL | polycaprolactone |
| Pd(PPh$_3$)$_4$ | tetrakis(triphenylphosphino)-palladium(0) |
| PL | polylactide |
| PLLA | poly(L-lactide) |
| PS | polystyrene |
| RT | room temperature |
| s (NMR spectrum) | singlet |
| sh | shoulder |
| solv. | solvent |
| TEA | triethylamine |
| TGA | thermogravimetric analysis |
| THF | tetrahydrofuran |
| TLC | thin-layer chromatography |
| tr (NMR spectrum) | triplet |
| z | charge number |

Example 1

1. N,N'-Bis(2,6-diisopropylphenyl)-1,6,7,12-tetrachloro-3,4,9,10-perylenetetracarboxylic acid diimide

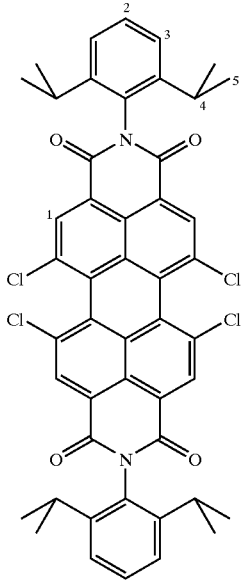

10 g (0.019 mol) of 1,6,7,12-tetrachloroperylene-3,4,9,10-tetracarboxylic acid dianhydride, 16.67 g (0.094 mol) of 2,6-diisopropylaniline and 250 ml of propionic acid are heated at the boil for 17 hours under argon in a 500 ml round-bottomed flask with reflux condenser, the mixture is cooled to room temperature, and the solid formed is subsequently filtered off via a D4 glass frit. The residue is rinsed in portions with 2 l of water/methanol (1:3) and dried overnight at 75° C. in a vacuum drying oven.

Yield: 13.61 g (84.4%) of orange-red solid Melting point: >300° C. $^1$H-NMR spectrum (250 MHz, $C_2D_2Cl_4$, 25° C.): δ (ppm)=8.11 (s, 4H, H-1), 7.34 (tr, $^3J$=7.6 Hz, 2H, H-2), 7.18 (d, $^3J$=7.6 Hz, 4H, H-3), 2.63 (h, $^3J$=7.1 Hz, 4H, H-4), 1.10 (d, $^3J$=7.1 Hz, 24H, H-5) $^{13}$C-NMR spectrum (spin echo experiment, 62.5 MHz, $C_2D_2Cl_4$, 25° C.): δ (ppm)= 162.50 (C=O), 145.82 (arom. q), 135.86 (arom. q), 133.61 (arom. CH), 131.94 (arom. q), 130.25 (arom. q), 130.04 (arom. CH), 129.14 (arom. q), 124.53 (arom. CH), 124.2 (arom. q), 123.47 (arom. q), 29.52 ($CH_{isopropyl}$), 24.44 ($CH_{3\ isopropyl}$). FD mass spectrum (8 kV): m/e (u $e_0^{-1}$)= 846.0 (100%, M$^+$) (calc.: 846.16) IR spectrum: ν=1701 ($ν_{C=O}$), 1654 ($ν_{C=O}$), 1579, 1353, 1279, 1204, 878 cm$^{-1}$ Elemental Analysis:

| $C_{48}H_{38}Cl_4N_2O_4$ | C | H | N |
|---|---|---|---|
| calculated | 67.93% | 4.51% | 3.30% |
| found | 67.88% | 4.45% | 3.41% |

2. N,N'-Bis(2,6-diisopropylphenyl)-1,6,7,12-tetra-[4-(2-hydroxyethyl)phenoxy]perylene-3,4,9,10-tetracarboxylic acid diimide

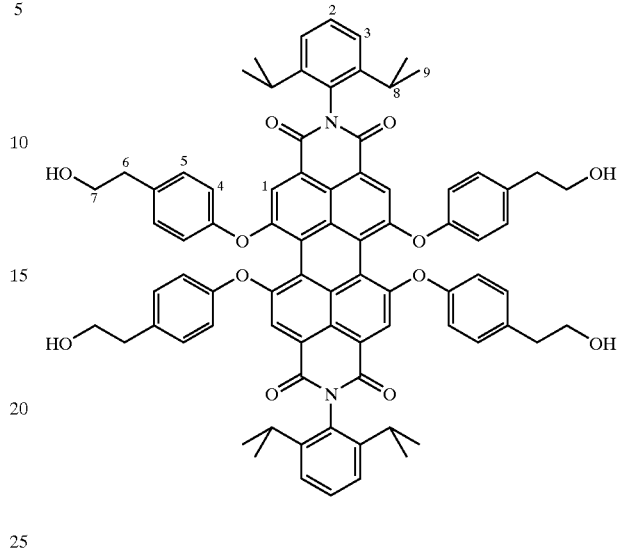

5 g (0.006 mol) of N,N'-bis(2,6-diisopropylphenyl)-1,6,7,12-tetrachloro-3,4,9,10-perylenetetracarboxylic acid diimide (1), 8.14 g (0.060 mol) of 4-hydroxyphenethyl alcohol and 4.07 g (0.029 mol) of $K_2CO_3$ in 250 ml of NMP are stirred for 12 hours at 90° C. under an argon atmosphere in a 500 ml round-bottomed flask. The reaction mixture is cooled to room temperature, poured into 1 l of a mixture of 0.5 part of $H_2O$, 4 parts of methanol and 0.2 part of conc. HCl, stirred for about 2 hours and subsequently filtered via a D4 glass frit. The solid obtained is dried at 60° C. under reduced pressure and subsequently purified by chromatography on silica gel with $CH_2Cl_2$/acetone in the ratio 1:1.

Yield: 5.56 g (75%) of dark-red solid Melting point: >300° C. $^1$H-NMR spectrum (300 MHz, $C_2D_2Cl_4$, 25° C.): δ (ppm)=8.14 (s, 4H, H-1), 7.33 (tr, $^3J$=9.2 Hz, 2H, H-2), 7.18 (d, $^3J$=9.2 Hz, 4H, H-3), 7.03 (d, $^3J$=9.0 Hz, 8H, H-5), 6.89 (d, $^3J$=9.1 Hz, 8H, H-4), 3.69 (tr, $^3J$=7.2 Hz, 8 H, H-7), 2.70 (tr, $^3J$=7.2 Hz, 8H, H-6), 2.60 (h, $^3J$=7.6 Hz, 4H, H-8), 1.06 (d, $^3J$=7.6 Hz, 24 H, H-9) $^{13}$C-NMR spectrum (spin echo experiment, 75 MHz, $C_2D_2Cl_4$, 25° C.) δ (ppm)= 163.71 (C=O), 156.04 (arom. q), 154.06 (arom. q), 145.69 (arom. q), 135.30 (arom. q), 133.57 (arom. q), 130.67 (arom. CH), 130.63 (arom. q), 129.68 (arom. CH), 129.65 (arom. CH), 124.20 (arom. CH), 122.87 (arom. q), 121.09 (arom. q), 120.53 (arom. q), 120.29 (arom. CH), 63.53 ($CH_2OH$), 38.58 ($CH_2$), 29.43 ($CH_{isopropyl}$), 24.05 ($CH_{3\ isopropyl}$) FD mass spectrum: m/e (u $e_0^{-1}$)=1255.4 (100%, M$^+$) (calc.: 1255.45) IR spectrum: ν=2962, 2868, 1704 ($ν_{C=O}$), 1665 ($ν_{C=O}$), 1585, 1501, 1407, 1285, 1201, 1046, 877, 572 cm$^{-1}$ UV spectrum (CHCl$_3$): $λ_{max}$ (ε)=449(15477), 538(28407), 580 nm (49579 1 mol$^{-1}$ cm$^{-1}$) Fluorescence spectrum (CHCl$_3$): λ max=611 nm Elemental Analysis:

| $C_{80}H_{74}N_2O_{12}$ | C | H | N |
|---|---|---|---|
| calculated | 62.45% | 3.78% | 4.05% |
| found | 61.62% | 3.77% | 3.94% |

3. N,N'-Bis(2,6-diisopropylphenyl)-1,6,7,12-tetra[4-(2-(N-butoxycarbonyl)aminoethyl)phenoxy]perylene-3,4,9,10-tetracarboxylic acid diimide

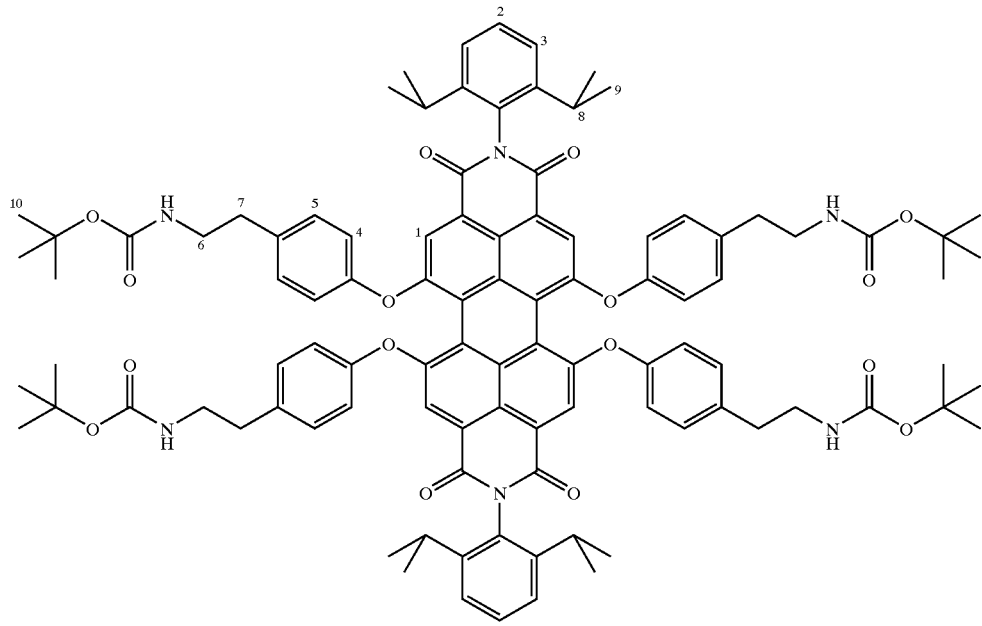

5 g (5.9 mmol) of N,N'-bis(2,6-diisopropylphenyl)-1,6,7,12-tetrachloro-3,4,9,10-perylenetetracarboxylic acid diimide (1), 13.98 g (0.0589 mol) of N-butoxycarbonyl(4-hydroxyphenyl)ethylamine and 6.08 g (0.044 mol) of $K_2CO_3$ in 250 ml of NMP are reacted analogously to 2. in a 500 ml round-bottomed flask. For work-up, the reaction mixture is poured into 1 l of a mixture of 4 parts of methanol and one part of 5% aqueous citric acid, stirred for about 2 hours and subsequently filtered via a D4 glass frit. The solid obtained is dried at 60° C. under reduced pressure and subsequently purified by chromatography on silica gel with $CH_2Cl_2$/acetone in the ratio 1:1.

Yield: 7.02 g (72%) of dark-red solid Melting point: 241–242° C. (with decomposition) $^1$H-NMR spectrum (300 MHz, $C_2D_2Cl_4$, 25° C.): δ (ppm)=8.15 (s, 4H, H-1), 7.32 (tr, $^3J$=8.2 Hz, 2H, H-2), 7.17 (d, $^3J$=8.2 Hz, 4H, H-3), 7.00 (d, $^3J$=8.0 Hz, 8H, H-4), 6.86 (d, $^3J$=8.0 Hz, 8H, H-5), 4.60 (d, $^3J$=8.9 Hz, 4 H, H-6), 3.2 (s, NH), 2.62 (m, 12H, H-7 and H-8), 1.35 (s, 36H, H-10), 1.02 (d, $^3J$=5.9 Hz, 24 H, H-9) $^{13}$C-NMR spectrum (spin echo, 75 MHz, $C_2D_2Cl_4$, 25° C.): δ (ppm)=163.5 (C=O), 156.17 ($Cq_{tert\text{-}butyl}$), 156.04 (arom. q), 154.01 (arom. q), 145.71 (arom. q), 135.77 (arom. q), 133.49 (arom. q), 130.71 (arom. q), 130.40 (arom. CH), 129.62 (arom. CH), 124.17 (arom. CH), 122.89 (arom. CH), 121.04 (arom. q), 120.49 (arom. q), 120.42 (arom. q), 120.25 (arom. CH), 79.44 ($Cq_{tert\text{-}butyl}$), 42.14 ($CH_2NH_2$), 35.78 ($CH_3$ $_{tert\text{-}butyl}$), 29.30 ($CH_{isopropyl}$), 28.76 ($CH_2$), 24.39 ($CH_3$ $_{isopropyl}$) FD mass spectrum: m/e (u $e_0^{-1}$)=1650.3 (100%, M$^+$)(calc.: 1650.80) IR spectrum: ν=3371, 2965, 2930, 2869, 1703 ($v_{C=O}$), 1672 ($v_{C=O}$), 1586, 1501, 1285, 1165, 878, 540 cm$^{-1}$ UV spectrum (CHCl$_3$): $\lambda_{max}$ (ε)=449 (17984), 539 (30654), 579 nm (49747 1 mol$^{-1}$ cm$^{-1}$) Fluorescence spectrum (CHCl$_3$): λmax=611 nm
Elemental Analysis:

| $C_{100}H_{110}N_6O_{16}$ | C | H | N |
|---|---|---|---|
| calculated | 62.45% | 3.78% | 4.05% |
| found | 61.62% | 3.77% | 3.94% |

4. N,N'-Bis(2,6-diisopropylphenyl)-1,6,7,12-tetra[4-(2-aminoethyl)phenoxy]perylene-3,4,9,10-tetracarboxylic acid diimide

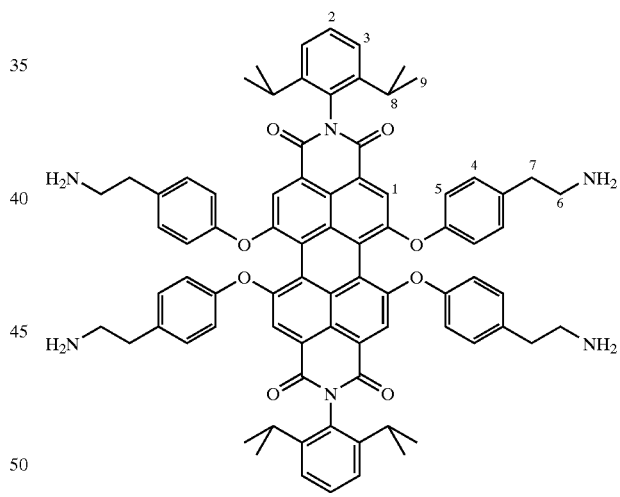

5 g (3.03 mmol) of N,N'-bis(2,6-diisopropylphenyl)-1,6,7,12-tetra[4-(2-(N-butoxycarbonyl)aminoethyl)phenoxy]perylene-3,4,9,10-tetracarboxylic acid diimide are dissolved in 50 ml of $CH_2Cl_2$ in a 100 ml flask and cooled to 0° C. using an ice/salt bath. 50 ml of trifluoroacetic acid are then slowly added dropwise via a dropping funnel, and the reaction mixture is stirred at low temperature for 1 hour. The mixture is then stirred at room temperature for a further 1 hour and evaporated to dryness in a rotary evaporator. The residue is dissolved in dioxane with addition of a little 25% aqueous ammonia solution and again evaporated to half the volume under reduced pressure. After further addition of 25% aqueous ammonia solution, the precipitate formed is filtered off via a D3 glass frit and rinsed twice with 25% aqueous ammonia solution and twice with water. The pulverulent residue is dried under a fine vacuum.

Yield: 3.72 g (98%) of dark-red solid Melting point: >300° C. $^1$H-NMR spectrum (500 MHz, CD$_2$Cl$_2$, 25° C.): δ (ppm)=8.18 (s, 4H, H-1), 7.44 (tr, $^3$J=8.2 Hz, 2H, H-2), 7.28 (d, $^3$J=8.2 Hz, 4H, H-3), 7.12 (d, $^3$J=8.8 Hz, 8H, H-4), 6.93 (d, $^3$J=8.7 Hz, 8H, H-5), 2.88 (tr, 3J=7.4 Hz, 8H, H-6), 2.68 (m, 12 H, H-7 and H-8), 1.41 (d, $^3$J=9.1 Hz, NH$_2$), 1.08 (d, $^3$J=6.4 Hz, 24 H, H-9) $^{13}$C-NMR spectrum (spin echo experiment, 125 MHz, CD$_2$Cl$_2$, 25° C.): δ (ppm)=163.7 (C=O), 156.35 (arom. q), 154.05 (arom. q), 146.37 (arom. q), 137.08 (arom. q), 133.59 (arom. q), 130.63 (arom. CH), 129.76 (arom. CH), 124.35 (arom. CH), 123.14 (arom. q), 121.18 (arom. q), 120.66 (arom. q), 120.39 (arom. CH), 120.19 (arom. CH), 43.97 (CH$_2$NH$_2$), 39.84 (CH$_2$), 29.43 (CH$_{isopropyl}$), 24.05 (CH$_{3\ isopropyl}$) FD mass spectrum: m/e (u e$_0^{-1}$)=1251.4 (100%, M$^+$) (calc.: 1250.59) IR spectrum: ν=3369 (NH$_2$), 3064, 2962, 2928, 2868, 1704 (ν$_{C=O}$), 1670 (ν$_{C=O}$), 1586, 1501, 1340, 1284, 1201, 878, 539 cm$^{-1}$ UV spectrum (CHCl$_3$): λ$_{max}$=612 nm
Elemental Analysis:

| C$_{80}$H$_{78}$N$_6$O$_8$ | C | H | N |
|---|---|---|---|
| calculated | 76.78% | 6.28% | 6.72% |
| found | 76.75% | 6.31% | 6.83% |

5. N,N'-Bis(4-bromo-2,6-diisopropylphenyl)-1,6,7,12-tetrachloro-3,4,9,10-tetracarboxylic acid diimide

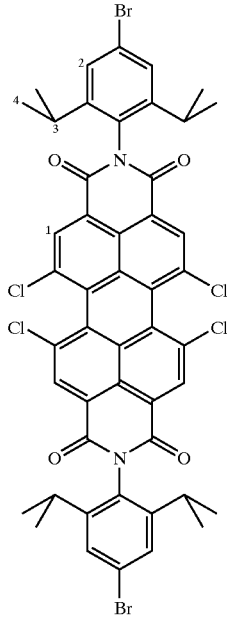

10 g (0.019 mol) of 1,6,7,12-tetrachloroperylene-3,4,9,10-tetracarboxylic dianhydride, 24.16 g (0.094 mol) of 4-bromo-2,6-diisopropylaniline and 250 ml of propionic acid are refluxed for 17 hours under argon in a 500 ml one-necked flask and cooled to room temperature, and the solid formed is subsequently filtered off via a D3 glass frit. The residue is washed in portions with 1 l of water/methanol (1:3) and dried overnight at 75° C. in a vacuum drying oven.

Yield: 15.4 g (80.53%) of orange-red solid Melting point: >300° C. $^1$H-NMR spectrum (250 MHz, C$_2$D$_2$Cl$_4$, 25° C.): δ (ppm)=8.68 (s, 4H, H-1), 7.28 (s, 4H, H-2), 2.61 (h, $^3$J=6.4 Hz, 4H, H-3), 1.18 (d, $^3$J=4.6 Hz, 24 H, H-4) $^{13}$C-NMR spectrum (spin echo experiment, 62.5 MHz, THF-d$_8$, 25° C.): δ (ppm)=162.89 (C=O), 149.59 (arom. q), 136.17 (arom q), 133.80 (arom. CH), 132.72 (arom. q), 130.80 (arom. q), 129.60 (arom. q), 128.27 (arom. CH), 125.34 (arom. q), 124.63 (arom. q), 110.21 (arom. q), 30.09 (CH$_{isopropyl}$) 24.03 (CH$_{3\ isopropyl}$) FD mass spectrum: m/e (u e$_0^{-1}$)=1001.4 (100%, M$^+$) (calc.: 1001.98) UV spectrum (CHCl$_3$): λ$_{max}$ (ε)=427 (11078), 488 (33922), 522 nm (49517 1 mol$^{-1}$ cm$^{-1}$) IR spectrum: ν=1704 (ν$_{C=O}$), 1663 (ν$_{C=O}$), 1585, 1401, 1356, 1301, 1201, 852 cm$^{-1}$
Elemental Analysis:

| C$_{48}$H$_{36}$Br$_2$Cl$_4$N$_2$O$_4$ | C | H | N |
|---|---|---|---|
| calculated | 57.28% | 3.61% | 2.78% |
| found | 57.41% | 3.63% | 2.75% |

6. N,N'-Bis(4-bromo-2,6-diisopropylphenyl)-1,6,7,12-tetra[4-(2-hydroxyethyl)phenoxy]perylene-3,4,9,10-tetracarboxylic acid diimide

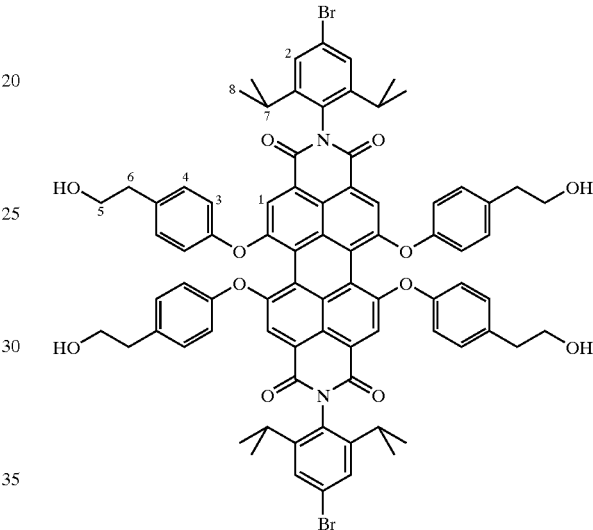

5 g (0.005 mol) of N,N'-bis(4-bromo-2,6-diisopropylphenyl)-1,6,7,12-tetrachloro-3,4,9,10-perylenetetracarboxylic acid diimide (5), 6.91 g (0.050 mol) of 4-hydroxyphenylethanol and 3.45 g (0.025 mol) of K$_2$CO$_3$ are stirred at 90° C. for 12 hours under argon in 250 ml of NMP. After a TLC check (eluent: CH$_2$Cl$_2$/acetone 1:1), the reaction mixture is poured into 1 l of a mixture of 0.5 art of water, 4 parts of methanol and 0.2 part of conc. hydrochloric acid, stirred for 2 hours and subsequently filtered via a D4 glass frit. The solid obtained is dried at 60° C. under reduced pressure and subsequently purified by chromatography on silica gel with CH$_2$Cl$_2$/acetone in the ratio 1:1.

Yield: 4.38 g (62%) of dark-red, pulverulent solid Melting point: >300° C. $^1$H-NMR spectrum (250 MHz, C$_2$D$_2$Cl$_4$, 25° C.) δ (ppm)=8.13 (s, 4H, H-1), 7.28 (s, 4H, H-2), 7.02 (d, $^3$J=7.7 Hz, 8 H, H-3), 6.87 (d, $^3$J=7.9 Hz, 8H, H-4), 3.69 (m, 12H, H-5 and OH), 2.70 (tr, $^3$J=7.8 Hz, 8H, H-6), 2.56 (h, $^3$J=7.1 Hz, 4 H, H-7), 1.01 (d, $^3$J=7.1, 24H, H-8) $^{13}$C-NMR spectrum (spin echo experiment, 62.5 MHz, C$_2$D$_2$Cl$_4$, 25° C.) δ (ppm)=163.37 (C=O), 156.22 (arom. q), 153.95 (arom. q), 148.38 (arom. q), 135.40 (arom. q), 133.55 (arom. q), 130.72 (arom. CH), 130.00 (arom. q), 127.66 (arom. CH), 123.88 (arom. q), 122.60 (arom. q), 121.21 (arom. q), 120.507 (arom. q), 120.38 (arom. CH), 120.26 (arom. CH), 63.52 (CH$_2$OH), 38.55 (CH$_2$), 29.44, 25.94 (CH$_{isopropyl}$), 24.22 (CH$_{3\ isopropyl}$) FD mass spectrum: m/e (u e$_0^{-1}$)=1410.4 (100% , M$^+$) (calc.: 1410.35) IR spectrum: ν=1704 (ν$_{C=O}$), 1684 (ν$_{C=O}$), 1672, 1586, 1500, 1408, 1341, 1311, 1284, 1201, 1051, 878 cm$^{-1}$ UV spectrum (CHCl$_3$): λ$_{max}$ (ε)=450 (15561), 541 (29261), 581 nm (49831 1 mol$^{-1}$ cm$^{-1}$)

Elemental Analysis:

| $C_{80}H_{72}Br_2N_2O_{12}$ | C | H | N |
|---|---|---|---|
| calculated | 67.99% | 5.14% | 1.98% |
| found | 67.83% | 5.30% | 1.79% |

7. N,N'-Bis[4-(butyn-1-ol)-2,6-diisopropylphenyl]-1,6,7,12-tetra[4-(4-hydroxyethyl)phenoxy]perylene-3,4,9,10-tetracarboxylic acid diimide

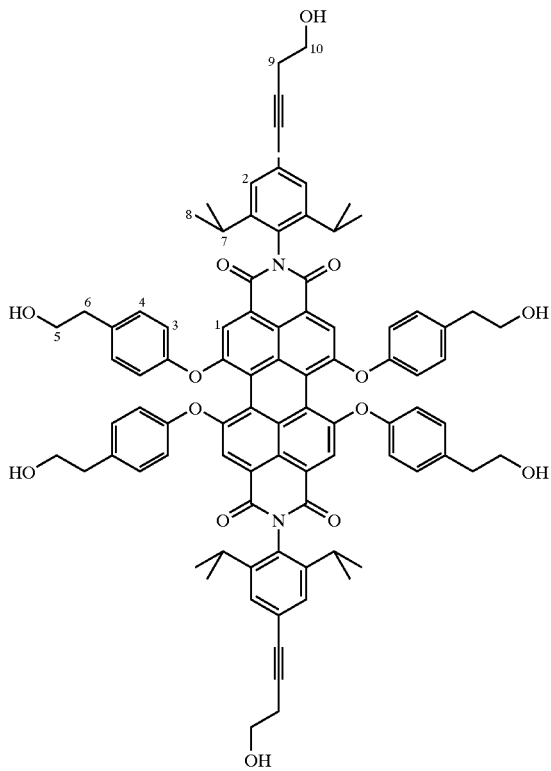

44 ml of THF and 44 ml of piperidine are mixed under an argon atmosphere in a 500 ml Schlenk flask. 3.00 g (2.12 mmol) of N,N'-bis(4-bromo-2,6-diisopropylphenyl)-1,6,7,12-tetra[4-(2-hydroxyethyl)phenoxy]perylene-3,4,9,10-tetracarboxylic acid diimide (6), 0.195 g (0.169 mmol) of Pd(PPh$_3$)$_4$ and 0.040 g (0.212 mmol) of copper(I) iodide are added in a counterstream of argon. The flask is sealed with a septum before 0.594 g (8.48 mmol) of butynol is added using a syringe and the reaction mixture is warmed to 50° C. After 24 hours, the temperature is increased to 80° C. After a further reaction time of 24 hours, the mixture is poured into a mixture of ice and conc. hydrochloric acid (3:1) and stirred for about 1 hour. The precipitated product is filtered off with suction via a D3 glass frit, dried in a fine vacuum and chromatographed on silica gel with CH$_2$Cl$_2$/ethanol (90:10).

Yield: 2.3 g (78%) of dark-red, pulverulent solid Melting point: >300° C. $^1$H-NMR spectrum (250 MHz, C$_2$D$_2$Cl$_4$, 25° C.): δ (ppm)=8.15 (s, 4H, H-1), 7.24 (s, 4H, H-2), 7.04 (d, $^3$J=7.8 Hz, 8H, H-3), 6.88 (d, $^3$J=7.9 Hz, 8H, H-4), 3.74 (m, 12H, H-5 and H-10), 2.67 (m, 16H, H-6, H-7, H-9), 1.02 (d, $^3$J=7.1 Hz, 24H, H-8) $^{13}$C-NMR spectrum (spin echo experiment, 75 MHz, C$_2$D$_2$Cl$_4$, 25° C.): δ (ppm)=163.4 (C=O), 156.16 (arom. q), 154.04 (arom q), 146.15 (arom. q), 135.29 (arom. q), 133.55 (arom. q), 130.72 (arom. CH), 127.84 (arom. q), 125.02 (arom. CH), 124.40 (arom. q), 122.74 (arom. q), 121.19 (arom. q), 120.55 (arom. q), 120.30 (arom. CH), 120.25 (arom. CH), 86.95 (C≡C), 82.98 (C≡C), 74.46 (CH$_2$), 63.52 (CH$_2$), 61.39 (CH$_2$), 38.53 (CH$_2$), 29.25 (CH$_{isopropyl}$), 24.26 (CH$_{3\ isopropyl}$) FD mass spectrum: m/e (u e$_0^{-1}$)=1391.5 (100%, M$^+$) (calc.: 1390.58) IR spectrum: ν=2961, 1726 (ν$_{C=O}$), 1689, 1582, 1502, 1468, 1334, 1295, 1200, 1045, 878 cm$^{-1}$ UV spectrum (CHCl$_3$): λ$_{max}$ (ε)=451 (15822), 539 (28988), 580 nm (49693 1 mol$^{-1}$ cm$^{-1}$) Fluorescence spectrum (CHCl$_3$): λ$_{max}$=610 nm

| $C_{88}H_{82}N_2N_2O_{14}$ | C | H | N |
|---|---|---|---|
| calculated | 75.95% | 5.94% | 2.01% |
| found | 75.17% | 6.08% | 1.89% |

8. N,N'-Bis(2,6-diisopropylphenyl)-1,6,7,12-tetra[4-(ethyl-2-(2-bromoisobutyrylamido)phenoxy]perylene-3,4,9,10-tetracarboxylic acid diimide

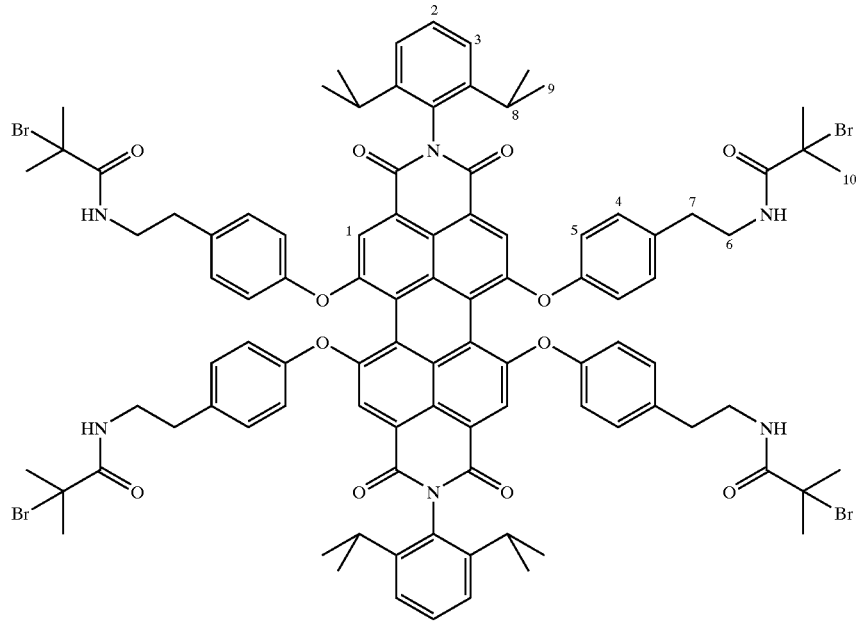

3.12 g (0.0025 mol) of N,N'-bis(2,6-diisopropylphenyl)-1,6,7,12-tetra[4-(2-aminoethyl)phenoxy]perylene-3,4,9,10-tetracarboxylic acid diimide (4) and 0.3 g (0.003 mol) of triethylamine are dissolved in 200 ml of dry $CH_2Cl_2$ in a 500 ml three-necked flask with internal thermometer, placed under argon and cooled to 0° C. in an ice/salt bath. 7.4 g (0.032 mol) of 2-bromoisobutyryl bromide are subsequently added slowly dropwise via a dropping funnel at such a rate that the temperature does not rise. After a reaction time of 2 hours (check by TLC), the precipitate formed (triethylammonium bromide) is filtered off, and the filtrate is washed twice with dilute aqueous hydrochloric acid and twice with dilute aqueous sodium carbonate solution. The organic phase is separated off and dried over sodium sulfate, and the solvent is removed under reduced pressure. The product is chromatographed on silica gel with $CH_2Cl_2$ as eluent.

Yield: 4.2 g (91.2%) of dark-red solid Melting point: >300° C. $^1$H-NMR spectrum (250 MHz, $C_2D_2Cl_4$, 25° C.): δ (ppm)=8.78 (s, 4H, H-1), 8.00 (tr, $^3J=8.2$ Hz, 2H, H-2), 7.84 (d, $^3J=8.2$ Hz, 4H, H-3), 7.71 (d, $^3J=6.8$ Hz, 8H, H-4), 7.54 (d, $^3J=6.8$ Hz, 8H, H-5), 7.36 (tr, $^3J=8.0$ Hz, 4H, NH), 4.03 (s, 8H, H-6), 3.38 (tr, $^3J=7.9$ Hz, 8H, H-7), 3.26 (h, $^3J=7.8$ Hz, 4H, H-8), 2.51 (s, 24H, H-10), 1.69 (d, $^3J=8.0$ Hz, 24H, H-9) $^{13}$C-NMR spectrum (spin echo experiment, 62.5 MHz, $C_2D_2Cl_4$, 25° C.): δ (ppm)=172.13 ($C=O_{amide}$), 163.49 ($C=O_{imide}$), 156.25 (arom. q), 154.16 (arom. q), 145.70 (arom. q), 135.41 (arom. q), 133.47 (arom. q), 130.67 (arom. q), 130.57 (arom. CH), 129.64 (arom. CH), 124.21 (arom. CH), 122.89 (arom. q), 120.97 (arom. q), 120.33 (arom. CH), 120.45 (arom. CH), 63.05 ($C_{q\ isobromobutyrate}$), 42.00 ($CH_2$), 35.01 ($CH_2$), 32.72 ($CH_{3\ isobromobutyrate}$), 29.28 ($CH_{isopropyl}$), 24.43 ($CH_{3\ isopropyl}$) FD mass spectrum: m/e (u $e_0^{-1}$)=1842.8 (100%, M$^+$) (calc.: 1842.40) IR spectrum: ν=3031, 2963, 2868, 1704 ($ν_{C=O}$), 1665 ($ν_{C=O}$), 1585, 1503, 1407, 1284, 1202, 1056, 1015, 878 cm$^{-1}$ UV spectrum (CHCl$_3$): $λ_{max}$ (ε)=447 (16361), 537 (28035), 577 nm (46036 1 mol$^{-1}$ cm$^{-1}$) Fluorescence spectrum (CHCl$_3$): $λ_{max}$=614 nm Elemental Analysis:

| $C_{96}H_{98}Br_4N_6O_{12}$ | C | H | N |
|---|---|---|---|
| calculated | 62.41% | 5.35% | 4.55% |
| found | 61.92% | 5.51% | 4.65% |

9. N,N'-Bis(2,6-diisopropylphenyl)-1,6,7,12-tetra[4-(ethyl-2-(2-bromoisobutyryloxy)phenoxy]perylene-3,4,9,10-tetracarboxylic acid diimide

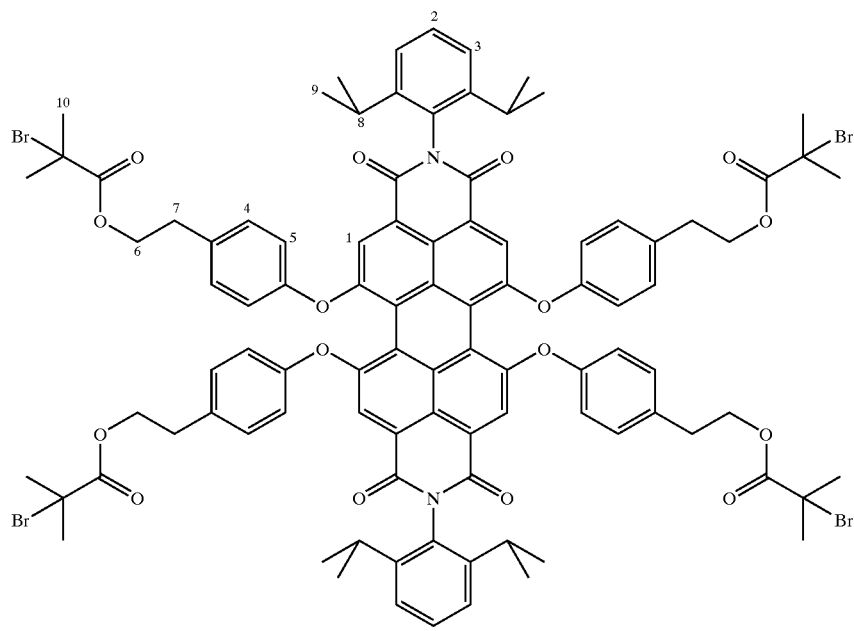

5 g (3.98 mmol) of N,N'-bis(2,6-diisopropylphenyl)-1,6,7,12-tetra[4-(4-hydroxyethyl)phenoxy]perylene-3,4,9,10-tetracarboxylic acid diimide (2) are reacted with 7.32 g (0.031 mol) of 2-bromoisobutyryl bromide with addition of 0.3 g (0.003 mol) of triethylamine analogously to 8.

Yield: 6.8 g (93%) of dark-red solid Melting point: >300° C. $^1$H-NMR spectrum (250 MHz, $C_2D_2Cl_4$, 25° C.): δ (ppm)=8.78 (s, 4H, H-1), 8.00 (tr, $^3J=8.2$ Hz, 2H, H-2), 7.84 (d, $^3J=8.2$ Hz, 4H, H-3), 7.71 (d, $^3J=6.8$ Hz, 8H, H-4), 7.54 (d, $^3J=6.8$ Hz, 8H, H-5), 4.03 (tr, $^3J=7.9$, 8H, H-6), 3.38 (tr, $^3J=7.9$ Hz, 8H, H-7), 3.26 (h, $^3J=7.9$ Hz, 4H, H-8), 2.51 (s, 24H, H-10), 1.69 (d, $^3J=7.9$ Hz, 24H, H-9) $^{13}$C-NMR spectrum (spin echo experiment, 125 MHz, $C_2D_2Cl_4$, 60° C.): δ (ppm)=172.97, 164.33, 157.09, 155.01, 146.54, 136.25, 134.25, 123.74, 121.82, 63.89, 42.84, 35.86 FD mass spectrum: m/e (u $e_0^{-1}$)=1846.8 (100%, M$^+$) (carc.: 1846.33) UV spectrum (CHCl$_3$): $λ_{max}$ (ε)=448 (20187), 537 (35699), 577 nm (58861 1 mol$^{-1}$ cm$^{-1}$) Fluorescence spectrum (CHCl$_3$): $λ_{max}$=614 nm IR spectrum: ν=2949, 1741 ($ν_{C=O}$), 1666 ($ν_{C=O}$), 1591 ($ν_{C=O}$), 1499, 1356, 1336, 1264, 1114, 820, 737 cm$^{-1}$ Elemental Analysis:

| $C_{96}H_{94}Br_4O_{16}$ | C | H | N |
| --- | --- | --- | --- |
| calculated | 62.98% | 5.12% | 1.51% |
| found | 62.92% | 5.16% | 1.53% |

10. N,N'-Bis(2,6-diisopropylphenyl)-1,7-di[4-(2-(N-butoxycarbonyl)aminoethyl)phenoxy]perylene-3,4,9,10-tetracarboxylic acid diimide

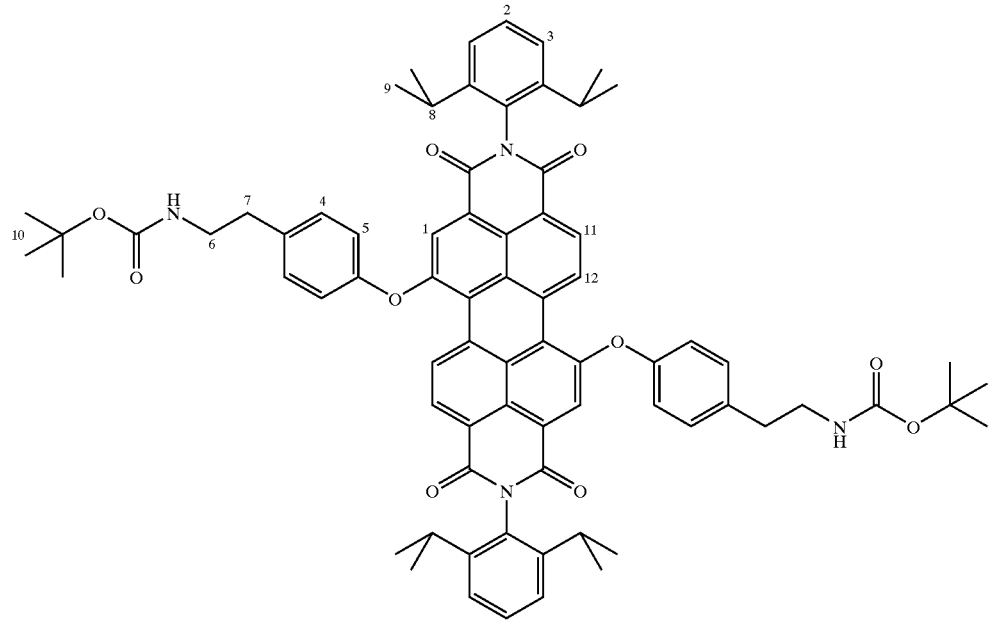

Analogously to 3., 6 g (6.9 mmol) of N,N'-bis(2,6-diisopropylphenyl)-1,7-dibromo-3,4,9,10-perylenetetracarboxylic acid diimide, 5.545 g (23.4 mmol) of BOC-protected tyramine and 2.42 g (17.5 mmol) of $K_2CO_3$ are reacted in 250 ml of NMP.

Yield: 4.5 g (55.2%) of orange solid having significant solid fluorescence Melting point: 284–285° C. (decomposition) $^1$H-NMR spectrum (250 MHz, $C_2D_2Cl_4$, 25° C.): δ (ppm)=9.65 (d, $^3J$=7.9 Hz, 2H, H-11), 8.66 (d, $^3J$=7.9 Hz, 2H, H-12), 8.38 (s, 2H, H-1), 7.48 (tr, $^3J$=6.9 Hz, 2H, H-2), 7.33 (d, $^3J$=8.2 Hz, 4H, H-3), 7.32 (d, $^3J$=8.2 Hz, 4H, H-4), 7.15 (d, $^3J$=6.9 Hz, 4H, H-5), 3.31 (tr, $^3J$=9.3 Hz, 4H, H-6), 2.75 (tr, $^3J$=9.3 Hz, 4H, H-7), 2.60 (h, $^3J$=8.2 Hz, 4H, H-8), 1.70 (s, NH), 1.34 (s, 18H, H-9), 1.05 (tr, $^3J$=8.2 Hz, 24H, H-10) $^{13}$C-NMR spectrum (spin echo experiment, 75 MHz, $C_2D_2Cl_4$, 25° C.): δ (ppm)=163.62 (C=O), 163.22 (C=O), 156.07 (C=O), 155.73 (arom. q), 153.62 (arom. q), 145.75 (arom. q), 136.59 (arom. q), 134.02 (arom. q), 131.20 (arom. CH), 130.99 (arom. CH), 130.73 (arom. q), 129.94 (arom. q), 129.73 (arom. CH), 129.29 (arom. CH), 125.93 (arom. q), 124.40 (arom. q), 124.30 (arom. CH), 124.17 (arom. CH), 124.10 (arom. q), 122.48 (arom. q), 120.06 (arom. CH), 79.51 ($C_{q\ tert-butyl}$), 42.07 ($CH_2NH_2$), 35.97 ($CH_{3\ tert-butyl}$), 29.40 ($CH_{isopropyl}$), 28.73 ($CH_2$), 24.39 ($CH_{3\ isopropyl}$) FD mass spectrum: m/e (u $e_0^{-1}$)=1180.5 (100%, M$^+$) (calc.: 1181.42) UV spectrum (CHCl$_3$): $\lambda_{max}$ (ε)=401 (9375), 509 (34332), 541 nm (45726 l mol$^{-1}$ cm$^{-1}$) IR spectrum: ν=3353, 3059, 2960, 2923, 2859, 1701 ($\nu_{C=O}$), 1659 ($\nu_{C=O}$), 1586, 1353, 1298, 1270, 872, 815 cm$^{-1}$ Fluorescence spectrum (CHCl$_3$): $\lambda_{max}$=578, 617 (sh) nm Elemental Analysis:

| $C_{74}H_{76}N_4O_{10}$ | C | H | N |
| --- | --- | --- | --- |
| calculated | 75.23% | 6.48% | 4.74% |
| found | 75.14% | 6.51% | 4.71% |

11. N,N'-Bis(2,6-diisopropylphenyl)-1,7-di[4-(2-aminoethyl)phenoxy]perylene-3,4,9,10-tetracarboxylic acid diimide

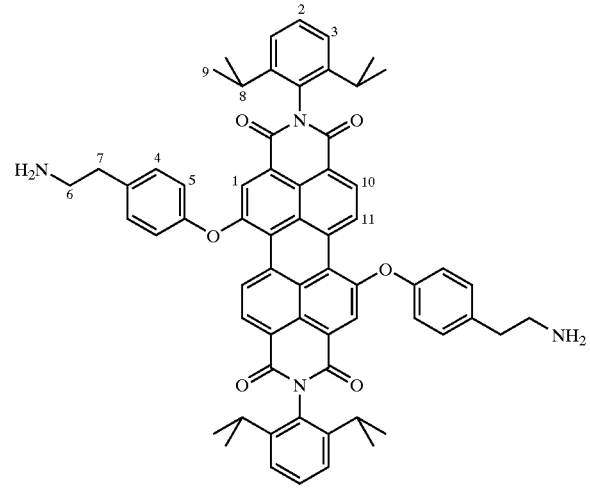

Analogously to 4., 5 g (4.2 mmol) of N,N'-bis(2,6-diisopropylphenyl)-1,7-di[4-(2-(N-butoxycarbonyl)

aminoethyl)phenoxy]perylene-3,4,9,10-tetracarboxylic acid diimide are reacted with 50 ml of trifluoroacetic acid in 50 ml of $CH_2Cl_2$.

Yield: 4.03 g (97%) of orange solid having significant solid fluorescence Melting point: 291–293° C. $^1$H-NMR spectrum (250 MHz, $C_2D_2Cl_4$, 25° C.): δ (ppm)=9.64 (d, $^3$J=8.4 Hz, 2H, H-1), 8.66 (d, $^3$J=8.4 Hz, 2H, H-11), 8.32 (s, 2H, H-1), 7.48 (tr, $^3$J=7.6 Hz, 2H, H-2), 7.34 (d, $^3$J=8 Hz, 2H, H-3), 7.32 (d, $^3$J=8 Hz, 4H, H-4), 7.15 (d, $^3$J=8 Hz, 4H, H-5), 2.97 (tr, $^3$J=6.9 Hz, 4H, H-6), 2.77 (tr, $^3$J=6.9 Hz, 4H, H-7), 2.71 (h, $^3$J=7.4 Hz, 4H, H-8), 1.11 (s, 24H, H-9) $^{13}$C-NMR spectrum (spin echo experiment, 75 MHz, $C_2D_2Cl_4$, 25° C.): δ (ppm)=163.62 (C═O), 163.22 (C═O), 155.73 (arom. q), 153.62 (arom. q), 145.75 (arom. q), 136.59 (arom. q), 134.02 (arom. q), 131.20 (arom. CH), 130.99 (arom. CH), 130.73 (arom. q), 129.94 (arom. q), 129.73 (arom. CH), 129.29 (arom. CH), 125.93 (arom. q), 124.40 (arom. q), 124.30 (arom. CH), 124.17 (arom. CH), 124.10 (arom. q), 122.48 (arom. q), 120.06 (arom. CH), 43.46 ($CH_2NH_2$), 38.68 ($CH_2$), 29.40 ($CH_{isopropyl}$), 24.39 ($CH_3$ $_{isopropyl}$) FD mass spectrum: m/e (u $e_0^{-1}$)=981.0 (100%, M$^+$) (calc.: 981.18) UV spectrum ($CHCl_3$): $\lambda_{max}$ (ε)=402 (8665), 511 (31350), 543 nm (43466 l mol$^{-1}$ cm$^{-1}$) IR spectrum: ν=3353, 2961, 2923, 2867, 1707 ($\nu_{C═O}$), 1665 ($\nu_{C═O}$), 1593, 1502, 1405, 1335, 1260, 1197, 812 cm$^{-1}$ Fluorescence spectrum ($CHCl_3$): $\lambda_{max}$=578, 617 (sh) nm
Elemental Analysis:

| $C_{64}H_{60}N_4O_6$ | C | H | N |
|---|---|---|---|
| calculated | 78.34% | 6.16% | 5.71% |
| found | 78.94% | 6.21% | 5.68% |

12. N,N'-Bis(2,6-diisopropylphenyl)-1,7-di[4-(2-hydroxyethyl)phenoxy]perylene-3,4,9,10-tetracarboxylic acid diimide

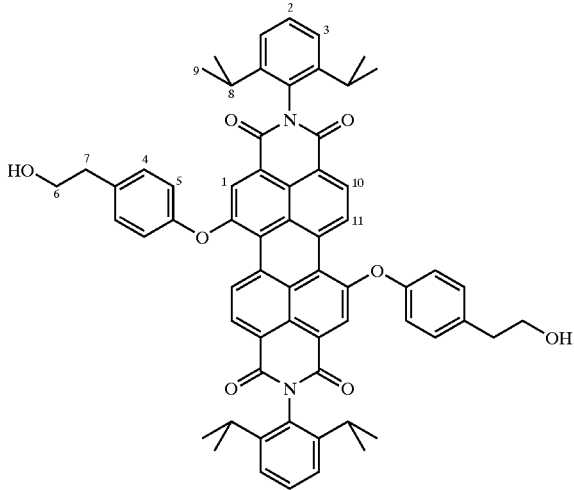

Analogously to 2., 5 g (5.7 mmol) of N,N'-bis(2,6-diisopropylphenyl)-1,7-dibromoperylene-3,4,9,10-tetracarboxylic acid diimide are reacted with 3.18 g (0.023 mol) of 4-hydroxyphenyl alcohol.

Yield: 3.42 g (61%) of orange solid having significant solid fluorescence Melting point: 291–293° C. $^1$H-NMR spectrum (250 MHz, $C_2D_2Cl_4$, 25° C.): δ (ppm)=9.54 (d, $^3$J=8.2 Hz, 2H, H-1), 8.62 (d, $^3$J=8.2 Hz, 2H, H-10), 8.2 (s, 2H, H-11), 7.38 (tr, $^3$J=7.9 Hz, 2H, H-2), 7.32 (d, $^3$J=8 Hz, 2H, H-3), 7.29 (d, $^3$J=8.4 Hz, 4H, H-4), 7.13 (d, $^3$J=8.4 Hz, 4H, H-5), 3.81 (tr, $^3$J=8.4 Hz, 4H, H-6), 2.82 (tr, $^3$J=6.9 Hz, 4H, H-7), 2.61 (h, $^3$J=6.9 Hz, 4H, H-8), 1.05 (s, 24H, H-9) $^{13}$C-NMR spectrum (spin echo experiment, 75 MHz, $C_2D_2Cl_4$, 25° C.): δ (ppm)=163.66 (C═O), 163.27 (C═O), 155.79 (arom. q), 153.56 (arom. q), 145.75 (arom. q), 136.25 (arom. q), 134.05 (arom. q), 131.45 (arom. CH), 131.01 (arom. CH), 130.70 (arom. q), 129.95 (arom. q), 129.76 (arom. CH), 129.31 (arom. CH), 125.91 (arom. q), 124.38 (arom. CH), 124.31 (arom. CH), 124.05 (arom. q), 122.45 (arom. q), 120.12 (arom. CH), 63.70 ($CH_2OH$), 38.74 ($CH_2$), 29.39 ($CH_{isopropyl}$), 24.37 ($CH_3$ $_{isopropyl}$) FD mass spectrum: m/e (u $e_0^{-1}$)=981.0 (100%, M$^+$) (calc.: 981.18) UV spectrum ($CHCl_3$): $\lambda_{max}$ (ε)=401 (10578), 544 nm (49482 l mol$^{-1}$ cm$^{-1}$) IR spectrum: ν=2961, 2923, 2868, 1705 ($\nu_{C═O}$), 1664 ($\nu_{C═O}$), 1593, 1502, 1406, 1336, 1260, 1197, 1055, 812 cm$^{-1}$ Fluorescence spectrum ($CHCl_3$): $\lambda_{max}$=579, 615 (sh) nm
Elemental Analysis:

| $C_{64}H_{58}N_2O_8$ | C | H | N |
|---|---|---|---|
| calculated | 78.19% | 5.95% | 2.85% |
| found | 78.13% | 5.97% | 2.82% |

13. tert-Amylcaprolactone

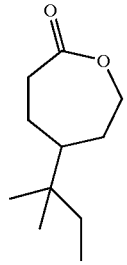

1 l of $CH_2Cl_2$, 10.5 g (0.0715 mol) of trifluoromethanesulfonic acid as catalyst and 212.6 g (60%=1.45 mol) of m-chloroperoxybenzoic acid are introduced into a 2 l flask. The mixture is cooled to 0° C. in a cooling bath, and 120 g (0.7 mol) of 4-tert-amylcyclohexanone are rapidly added dropwise with vigorous stirring, during which the temperature should not exceed 20° C. When the addition is complete, the mixture is stirred for a further 30 minutes without the cooling bath. The solid residue (4-chlorobenzoic acid) is subsequently filtered off via a glass frit. The filtrate is washed firstly with 1 l of 5% aqueous sodium hydrogencarbonate solution and then with saturated, aqueous sodium chloride solution. The dichloromethane is distilled off in a rotary evaporator, and the yellowish, oily residue is dried in a fine vacuum. For rigorous removal of traces of water, the product is stirred overnight at 100° C. with calcium hydride and subsequently distilled over a 25 cm Vigreux column.

Yield: 125.1 g (97%) (after distillation 93.8 g (86%)) of white solid Melting point: 42–45° C. Boiling point: 110° C. (2*10$^{-3}$ mbar) $^1$H-NMR spectrum (500 MHz, $C_2D_2Cl_4$, 353 K): δ (ppm)=4.08 (m, 1H), 3.94 (m, 1H), 2.40 (m, 2H), 1.80 (m, 1H), 1.73 (m, 1H), 1.25 (m, 2H), 1.1 (m, 3H), 0.65 (m, 9H) $^{13}$C-NMR spectrum (500 MHz, $C_2D_2Cl_4$, 353 K): δ (ppm)=175.19, 68.13, 47.7, 34.88, 33.28, 32.12, 29.87, 23.89, 23.85, 23.23, 7.69

Elemental Analysis:

| $C_{11}H_{20}O_2$ | C | H |
|---|---|---|
| calculated | 71.70% | 10.94% |
| found | 71.71% | 10.97% |

14. Polymerizations

The UV/VIS and fluorescence spectra of the polymers are in each case identical to those of the corresponding dyes with a deviation of +/−2 nm. For each type of polymer, a $^1$H-NMR spectrum is indicated. The spectra of the respective analogous polymers differ merely through the integration numbers, which are reflected directly in the $^1$H-NMR DP data. The yields in the polymerizations are in all cases between 95 and 98%.

14.1. General Working Procedure for Ring-opening Living Polymerization of Polylactides Illustrative Procedure:

225 mg (0.20 mmol) of the initiator-dye molecule and 1.44 g (0.02 mol) of L,L-dilactide are weighed into a Schlenk tube in a glove box. The Schlenk tube is sealed using a septum, removed from the glove box and warmed to 90° C. in an oil bath under argon. When all the monomer has melted, 6.4 mg (0.016 mmol) of tin(II) (2-ethyl)hexanoate in the form of a 1% solution in anhydrous toluene are injected as catalyst. The amount of catalyst corresponds to 1/50 of the molar amount of OH groups. The temperature is increased to 110° C., and the mixture is stirred for 48 hours. The polymer, which is then solid, is dissolved in $CH_2Cl_2$ and precipitated by dropwise addition to methanol with stirring, giving the polymer 1 a as a red powder in quantitative yield, which is subsequently dried in a fine vacuum.

1 b, 1 c and 2 a–c are obtained analogously, but using the amounts of initiator and monomer indicated in the table.

$^1$H-NMR spectrum of the 4-arm star polymer 1 a (300 MHz, $C_2D_2Cl_4$, 25° C.): δ (ppm)=8.08 (s, 4H), 7.32 (tr, 2H), 7.16 (d, 4H), 7.03 (d, 8H), 6.85 (d, 8H), 5.08 (m, 91H), 4.23 (m, 12H), 2.82 (s, 8H), 2.58 (tr, 6H), 1.49 (d, 254H), 1.00 (s, 24H) Illustrative $^1$H-NMR spectrum for 6-arm star polymers: $^1$H-NMR spectrum of the compound 2 a (250 MHz, $C_2D_2Cl_4$, 25° C.): δ (ppm)=8.10 (s, 4H), 7.20 (s, 4H), 7.04 (d, 8H), 6.84 (d, 8H), 5.10 (q, 143.8 H), 4.25 (m, 18H), 2.86 (d, 8H), 2.75 (h, 4H), 2.61 (tr, 4H), 1.50 (d, 447H), 1.00 (s, 24 H)

14.1.1. PLLA 1 a–c

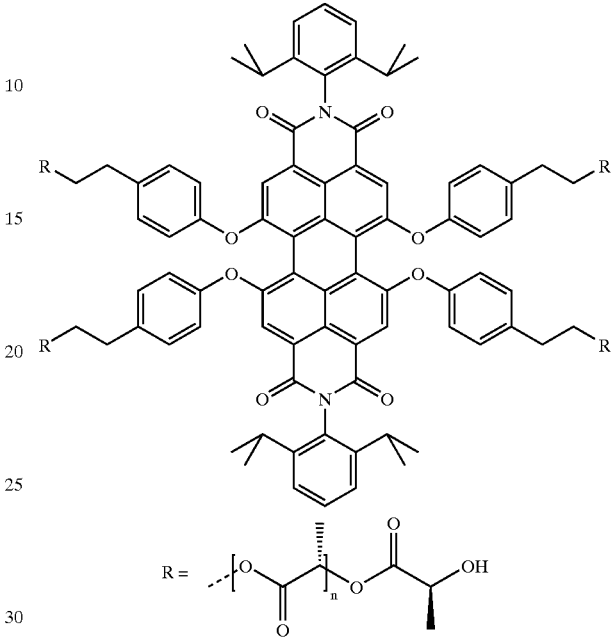

TABLE 1

| No. | DP, target | Initiator | Monomer | Catalyst |
|---|---|---|---|---|
| 1 a | 25 | 225 mg<br>0.20 mmol | 1.44 g<br>0.02 mol | 6.4 mg<br>0.016 mmol |
| 1 b | 50 | 225 mg<br>0.20 mmol | 2.88 g<br>0.04 mol | 6.4 mg<br>0.016 mmol |
| 1 c | 100 | 112.5 mg<br>0.10 mmol | 2.88 g<br>0.04 mol | 3.2 mg<br>0.008 mmol |

Characterization:

TABLE 2

Characterization and thermal properties of the PLLA 4-arm stars produced

| No. | DP target | DP[1] | DP[2] | $M_n^3$ | DP[3] | $M_w/M_n^3$ | $M_n^4$ | DP[4] | $M_w/M_n^4$ | $T_g$ (° C.)[5] | m.p. (° C.)[5] | d.p. (° C.)[6] |
|---|---|---|---|---|---|---|---|---|---|---|---|---|
| 1 a | 25 | 22.7 | 22.5 | 10690 | 32.8 | 1.11 | 6821 | 19.3 | 1.07 | 55.4 | — | 290.9 |
| 1 b | 50 | 51.1 | 47.5 | 19630 | 63.7 | 1.11 | 11017 | 33.8 | 1.05 | 58.45 | 152.2 | 283.9 |
| 1 c | 100 | 105 | 93.4 | 39800 | 133.7 | 1.06 | 19929 | 64.8 | 1.04 | 59.8 | 159.4 | 277.8 |

[1]determined from $^1$H-NMR spectra, 300 MHz, $C_2D_2Cl_4$
[2]determined from UV/VIS spectra, chloroform, ε = 4.96 * 10$^4$ l/mol * cm
[3]determined from GPC elugrams, eluent: THF, calibration curve: polystyrene, 30° C.
[4]determined from MALDI-TOF mass spectra
[5]determined from DSC diagram, two heating curves, one cooling curve, −160° C.–300° C., heating rate: 10° C./min
[6]determined from TGA curve, 10° C./min, center point 14.1.2 PLLA 2 a–c

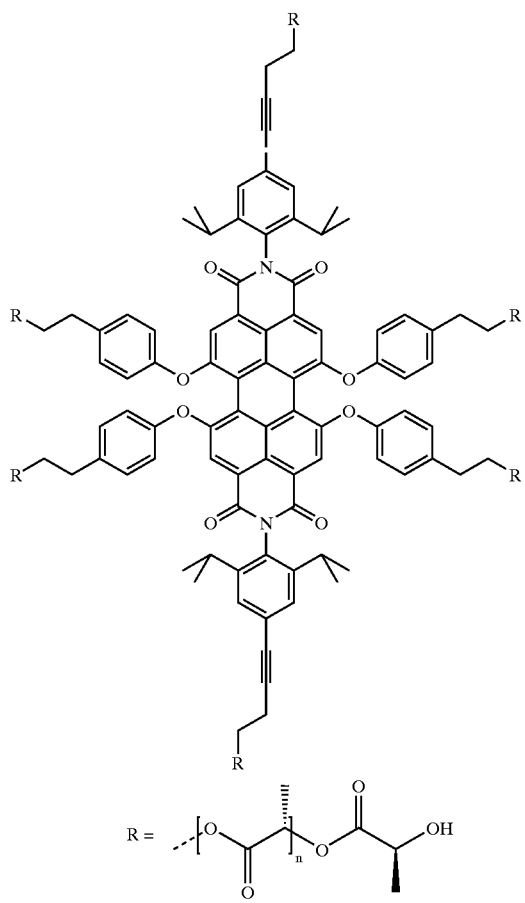

TABLE 3

| No. | DP, target | Initiator | Monomer | Catalyst |
|---|---|---|---|---|
| 2 a | 25 | 200 mg<br>0.14 mmol | 1.51 g<br>10.5 mol | 6.7 mg<br>0.017 mmol |
| 2 b | 50 | 200 mg<br>0.14 mmol | 3.03 g<br>21 mol | 6.7 mg<br>0.017 mmol |
| 2 c | 100 | 100 mg<br>0.07 mmol | 3.03 g<br>21 mol | 3.35 mg<br>0.008 mmol |

Characterization:

TABLE 4

Characterization and thermal properties of the PLLA 6-arm stars produced

| No. | DP target | $DP^1$ | $DP^2$ | $M_n^3$ | $DP^3$ | $M_w/M_n^3$ | $M_n^4$ | $DP^4$ | $M_w/M_n^4$ | $T_g$ (° C.)[5] | m.p. (° C.)[5] | d.p. (° C.)[6] |
|---|---|---|---|---|---|---|---|---|---|---|---|---|
| 2 a | 25 | 24 | 22 | 13560 | 28.1 | 1.12 | 10397 | 20.8 | 1.08 | 49.6 | — | 261.2 |
| 2 b | 50 | 54.7 | 48.5 | 28730 | 63.2 | 1.08 | 20515 | 44.2 | 1.06 | 50.3 | 147.0 | 248.3 |
| 2 c | 100 | 95.4 | 97.2 | 53720 | 121.0 | 1.06 | 38661 | 86.2 | 1.1 | 57.7 | 160.1 | 252.6 |

[1]determined from $^1$H-NMR spectra, 300 MHz, $C_2D_2Cl_4$
[2]determined from UV/VIS spectra, chloroform, $\epsilon = 4.96 * 10^4$ l/mol * cm
[3]determined from GPC elugrams, eluent: THF, calibration curve: polystyrene, 30° C.
[4]determined from MALDI-TOF mass spectra
[5]determined from DSC diagram, two heating curves, one cooling curve, −160° C.–300° C., heating rate: 10° C./min
[6]determined from TGA curve, 10° C./min, center point 14.2. General Working Procedure for Ring-opening Living Polymerization of Polycaprolactones Illustrative Procedure:

The monomer E-caprolactone is dried for 12 hours over calcium hydride, distilled and stored under $N_2$. Toluene is dried over potassium and distilled under dry argon.

225 mg (0.20 mmol) of the initiator-dye molecule are weighed into a Schlenk tube which has been dried by heating. The Schlenk tube is sealed using a septum and placed under argon, 2.28 g (0.02 mol) of e-caprolactone are injected through the septum using a syringe, and the mixture is heated at 90° C. in an oil bath. 6.4 mg (0.016 mmol) of $Sn(oct)_2$ in the form of a 1% solution in anhydrous toluene are injected as catalyst. The amount of catalyst corresponds to 1/50 of the molar amount of OH groups. The temperature is increased to 110° C., and the mixture is stirred for 48 hours. The polymer, which is then solid, is dissolved in $CH_2Cl_2$ and precipitated by dropwise addition to MeOH with stirring, giving the polymer 3 a as a red powder in quantitative yield, which is subsequently dried in a fine vacuum.

3 b–d and 4 a–d are obtained analogously, but using the amounts of initiator and monomer indicated in the table.

$^1$H-NMR spectrum of the 4-arm star polymer 3 a (300 MHz, $C_2D_2Cl_4$, 25° C.): δ (ppm)=8.16 (s, 4H), 7.36 (tr, 2H), 7.20 (d, 4H), 7.08 (d, 8H), 6.90 (d, 8H), 3.99 (tr, 203H), 3.56 (tr, 8H), 2.26 (tr, 210H), 1.58 (m, 427H), 1.13 (m, 218H), 1.06 (s, 24H) Illustrative $^1$H-NMR spectrum for 6-arm star polymers: $^1$H-NMR spectrum of the compound 4 b (250 MHz, $C_2D_2Cl_4$, 25° C.): δ (ppm)=8.11 (s, 4H), 7.20 (s, 4H), 7.03 (d, 8H), 6.83 (d, 8H), 3.94 (tr, 319.5H), 2.21 (tr, 333.8H), 1.53 (m, 761.7H), 1.28 (m, 348.5H), 1.00 (s, 24H)

14.2.1 PCL 3 a–d

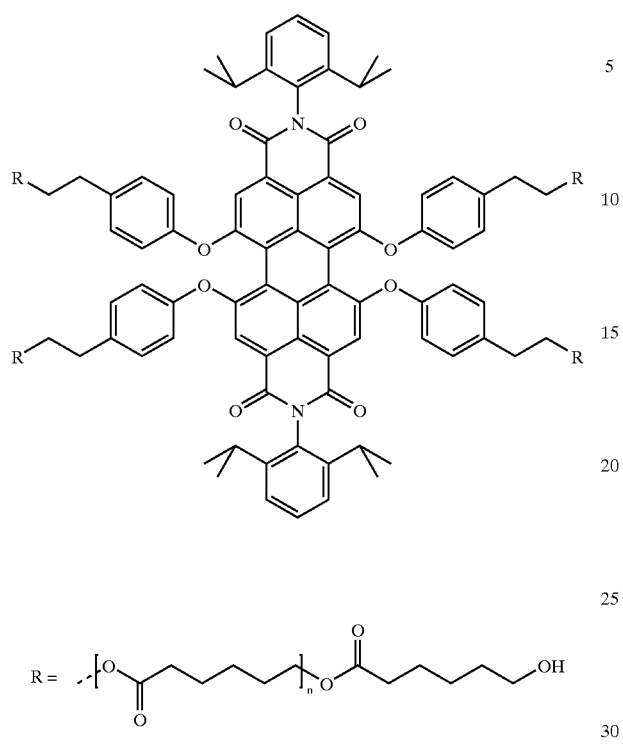

14.2.2 PCL 4 a–d

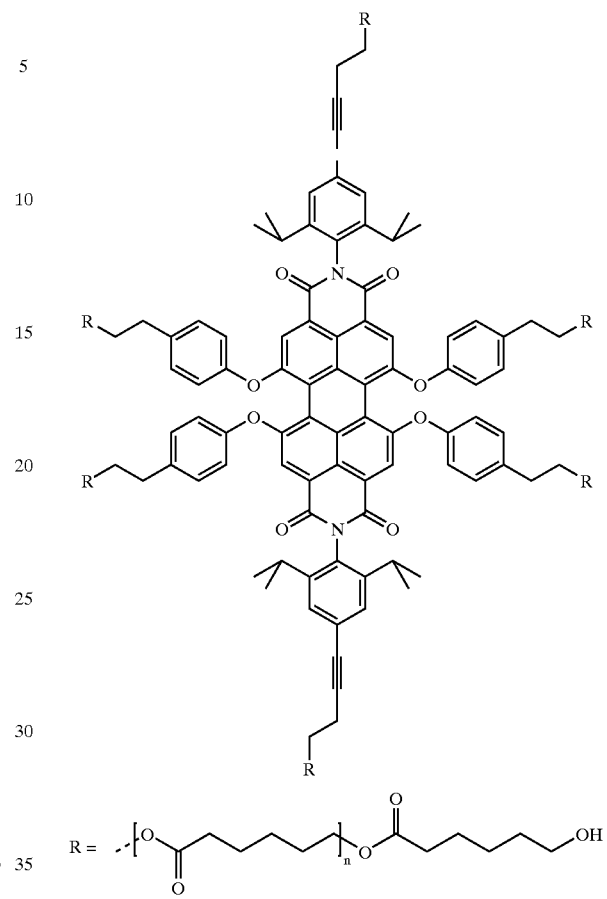

TABLE 5

| No. | DP, target | Initiator | Monomer | Catalyst |
|---|---|---|---|---|
| 3 a | 10 | 11.25 mg<br>0.01 mmol | 4.56 g<br>0.04 mol | 0.64 mg<br>0.016 mmol |
| 3 b | 25 | 225 mg<br>0.20 mmol | 2.28 g<br>0.02 mol | 6.4 mg<br>0.016 mmol |
| 3 c | 50 | 225 mg<br>0.20 mmol | 4.56 g<br>0.04 mol | 6.4 mg<br>0.016 mmol |
| 3 d | 100 | 112.5 mg<br>0.10 mmol | 4.56 g<br>0.04 mol | 3.2 mg<br>0.008 mmol |

TABLE 7

| No. | DP, target | Initiator | Monomer | Catalyst |
|---|---|---|---|---|
| 4 a | 10 | 10 mg<br>0.007 mmol | 0.78 g<br>4.2 mmol | 3.36 mg<br>0.008 mmol |
| 4 b | 25 | 200 mg<br>0.14 mmol | 2.40 g<br>21 mmol | 6.72 mg<br>0.017 mmol |
| 4 c | 50 | 200 mg<br>0.14 mmol | 3.03 g<br>42 mmol | 6.72 mg<br>0.017 mmol |
| 4 d | 100 | 100 mg<br>0.07 mmol | 7.8 g<br>42 mmol | 3.36 mg<br>0.008 mmol |

Characterization:

TABLE 6

Characterization and thermal properties of the PCL 4-arm stars produced

| No. | DP target | DP[1] | DP[2] | $M_n$[3] | DP[3] | $M_w/M_n$[3] | $M_n$[4] | DP[4] | $M_w/M_n$[4] | $T_g$ (°C.)[5] | m.p. (°C.)[5] | d.p. (°C.)[6] |
|---|---|---|---|---|---|---|---|---|---|---|---|---|
| 3 a | 10 | 9.5 | 10.6 | 9739 | 18.6 | 1.13 | 5008 | 8 | 1.08 | −52.6 | 39.36 | 338.1 |
| 3 b | 25 | 25.4 | 25.8 | 19820 | 40.7 | 1.1 | 11728 | 22.9 | 1.09 | — | 52.9 | 338.1 |
| 3 c | 50 | 36.5 | 35.2 | 25660 | 53.4 | 1.08 | 15603 | 31.4 | 1.02 | — | 53.6 | 348.8 |
| 3 d | 100 | 111 | 100.1 | 63000 | 135.2 | 1.07 | 37211 | 78.7 | 1.04 | — | 57.6 | 405.5 |

[1]determined from $^1$H-NMR spectra, 300 MHz, $C_2D_2Cl_4$
[2]determined from UV/VIS spectra, chloroform, $\epsilon = 4.96 * 10^4$ l/mol * cm
[3]determined from GPC elugrams, eluent: THF, calibration curve: polystyrene, 30° C.
[4]determined from MALDI-TOF mass spectra
[5]determined from DSC diagram, two heating curves, one cooling curve, −160° C.–300° C., heating rate: 10° C./min
[6]determined from TGA curve, 10° C./min, center point Characterization:

TABLE 8

Characterization and thermal properties of the PCL 4-arm stars produced

| No. | DP target | DP[1] | DP[2] | $M_n^3$ | DP[3] | $M_w/M_n^3$ | $M_n^4$ | DP[4] | $M_w/M_n^4$ | $T_g$ (°C.)[5] | m.p. (°C.)[5] | d.p. (°C.)[6] |
|---|---|---|---|---|---|---|---|---|---|---|---|---|
| 4 a | 10 | 10.7 | 8.7 | 7040 | 8.2 | 1.14 | 6669 | 7.7 | 1.09 | −52.7 | 38.5 | 304.2 |
| 4 b | 25 | 26.6 | 24.2 | 22480 | 30.8 | 1.16 | 15464 | 20.5 | 1.07 | — | 50.1 | 331.1 |
| 4 c | 50 | 60.4 | 49.7 | 36200 | 50.8 | 1.07 | 27292 | 37.8 | 1.05 | — | 53.5 | 325.0 |
| 4 d | 100 | 93.2 | 100.4 | 51880 | 73.7 | 1.11 | 41765 | 58.9 | 1.03 | — | 54.7 | 334.2 |

[1]determined from ¹H-NMR spectra, 300 MHz, $C_2D_2Cl_4$
[2]determined from UV/VIS spectra, chloroform, ε = 4.96 * 10⁴ l/mol * cm
[3]determined from GPC elugrams, eluent: THF, calibration curve: polystyrene, 30° C.
[4]determined from MALDI-TOF mass spectra
[5]determined from DSC diagram, two heating curves, one cooling curve, −160° C.–300° C., heating rate: 10° C./min
[6]determined from TGA curve, 10° C./min, center point

14.2.3 PACL 5 a–d

General Working Procedure: See Caprolactone

For work-up, the reaction mixture is poured into methanol and stirred for about 1 hour. The resultant suspension is centrifuged, the solvent is decanted off, and the polymer which remains is dried in a fine vacuum.

5 a–d are obtained analogously, but using the amounts of initiator and monomer indicated in the table.

¹H-NMR spectrum of the compound PACL 5 a: (300 MHz, $C_2D_2Cl_4$, 25° C.): δ (ppm)=8.12 (s, 4H), 7.32 (tr, 2H), 7.16 (d, 4H), 7.05 (d, 8H), 6.85 (d, 8H), 3.93 (m, 74H), 3.52 (tr, 8H), 2.82 (s, 8H), 2.59 (tr, 4H), 2.24 (m, 74H), 1.74 (tr, 74H), 1.23 (m, 148H), 0.98 (m, 60H), 0.73 (m, 332H)

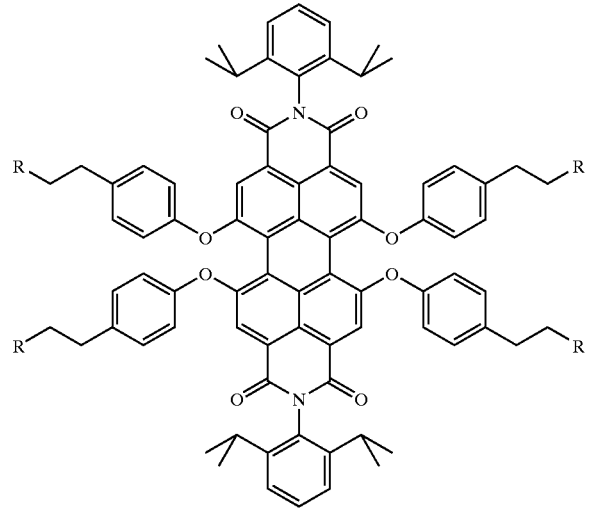

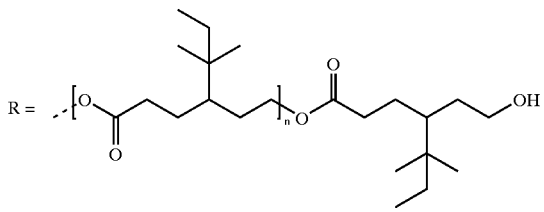

TABLE 9

| No. | DP, target | Initiator | Monomer | Catalyst |
|---|---|---|---|---|
| 5 a | 10 | 200 mg<br>0.14 mmol | 1.03 g<br>5.6 mmol | 4.48 mg<br>0.012 mmol |
| 5 b | 25 | 200 mg<br>0.14 mmol | 2.58 g<br>0.014 mol | 4.48 mg<br>0.012 mmol |
| 5 c | 50 | 100 mg<br>0.07 mmol | 2.58 g<br>0.014 mol | 2.24 mg<br>0.006 mmol |
| 5 d | 100 | 100 mg<br>0.07 mmol | 5.16 g<br>0.028 mol | 2.24 mg<br>0.006 mmol |

Characterization:

TABLE 10

Characterization and thermal properties of the PCL 4-arm stars produced

| No. | DP target | DP[1] | DP[2] | $M_n^3$ | DP[3] | $M_w/M_n^3$ | $M_n^4$ | DP[4] | $M_w/M_n^4$ | $T_g$ (°C.)[5] | m.p. (°C.)[5] | d.p. (°C.)[6] |
|---|---|---|---|---|---|---|---|---|---|---|---|---|
| 5 a | 10 | 9.2 | 8.1 | 8224 | 9.5 | 1.14 | 7220 | 7.9 | 1.04 | −13.3 | — | 293.6 |
| 5 b | 25 | 23.7 | 20 | 17670 | 22.3 | 1.16 | 15452 | 19.1 | 1.08 | −21.1 | — | 290.5 |

TABLE 10-continued

Characterization and thermal properties of the PCL 4-arm stars produced

| No. | DP target | $DP^1$ | $DP^2$ | $M_n^3$ | $DP^3$ | $M_w/M_n^3$ | $M_n^4$ | $DP^4$ | $M_w/M_n^4$ | $T_g$ (°C.)[5] | m.p. (°C.)[5] | d.p. (°C.)[6] |
|---|---|---|---|---|---|---|---|---|---|---|---|---|
| 5 c | 50 | 44 | 40.5 | 25280 | 32.6 | 1.07 | 21707 | 27.6 | 1.06 | −24.6 | — | 288.0 |
| 5 d | 100 | 92.1 | 83.2 | 42860 | 55.1 | 1.11 | 33760 | 43.9 | 1.05 | −24.4 | — | 298.7 |

[1]determined from $^1$H-NMR spectra, 300 MHz, $C_2D_2Cl_4$
[2]determined from UV/VIS spectra, chloroform, $\epsilon = 4.96 * 10^4$ l/mol * cm
[3]determined from GPC elugrams, eluent: THF, calibration curve: polystyrene, 30° C.
[4]determined from MALDI-TOF mass spectra
[5]determined from DSC diagram, two heating curves, one cooling curve, −160° C.–300° C., heating rate: 10° C./min
[6]determined from TGA curve, 10° C./min, center point 14.3. General Working Procedure for Atom Transfer Radical Polymerization Copper(I) bromide (CuBr), 2,2'-bipyridine (Bpy), monomer and initiator N,N'-bis[4-(butyn-1-ol)-2,6-diisopropylphenyl]-1,6,7,12-tetra[4-(ethyl-2-bromoisobutyramido)phenoxy]perylene-3,4,9,10-tetracarboxylic acid diimide are weighed into a dry Schlenk tube which has been dried by heating, and the tube is sealed using a septum. The [initiator]:[CuBr]:[Bpy] ratio is 1:1:2. Dry toluene can be added as solvent.

The reaction mixture is degassed by freezing, pumping and thawing, i.e. the contents of the Schlenk tube are firstly frozen in liquid nitrogen, the tube is then evacuated to a pressure of $<1 \cdot 10^{-3}$ mbar and subsequently allowed to thaw to room temperature. This cycle is repeated twice. The evacuated Schlenk tube is finally heated to 110° C. in an oil bath, and the reaction mixture is stirred at this temperature for 48 hours. The polymer 6 a formed is subsequently dissolved in $CH_2Cl_2$ and precipitated by dropwise addition of this solution to methanol with stirring. The fine powder is filtered off via a D4 glass frit and dried in a fine vacuum. 6 b–c and 7 a–b are obtained analogously, but using the amounts of initiator and monomer indicated in the table.

$^1$H-NMR spectrum of the compound PS 6 a (300 MHz, $C_2D_2Cl_4$, 25° C.): δ (ppm)=8.13 (s, 4H), 7.36 (d, 2H), 7.27 (tr, 4H), 7.04 (m, 2701H), 6.56 (m, 1710H), 1.84 (m, 951H), 1.42 (s, 1998H), 1.07 (s, 18H), 0.80 (m, 41H)

14.3.1 PS 6 a–c

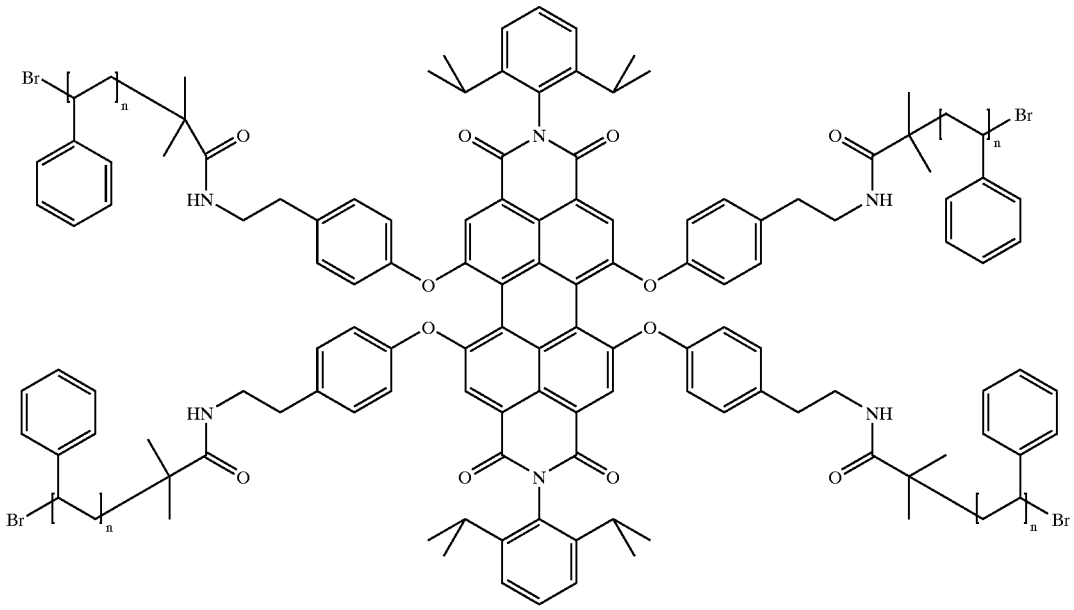

TABLE 11

| No. | Initiator | CuBr | Bpy | Monomer | Solv. | Conversion |
|---|---|---|---|---|---|---|
| 6 a | 300 mg 0.162 mmol | 93.0 mg 0.649 mmol | 0.202 g 1.3 mmol | 6.76 g 64.9 mmol | 3 ml toluene | 24.6% |
| 6 b | 300 mg 0.162 mmol | 93.0 mg 0.648 mmol | 0.202 g 1.3 mmol | 13.52 g 0.130 mol | — | 80.1% |
| 6 c | 300 mg 0.162 mmol | 93.0 mg 0.649 mmol | 0.202 g 1.3 mmol | 6.76 g 64.9 mmol | — | 70.4% |

Characterization:

TABLE 12

Characterization and thermal properties of the PCL 4-arm stars produced

| No. | DP target | $DP^1$ | $M_n^2$ | $DP^2$ | $M_w/M_n^2$ | $M_n^3$ | $DP^3$ | $M_w/M_n^3$ | $T_g$ (°C.)[4] | m.p. (°C.)[4] | d.p. (°C.)[5] |
|---|---|---|---|---|---|---|---|---|---|---|---|
| 6 a | 100 | 24.6 | 9594 | 18.6 | 1.24 | 9386 | 18.1 | 1.2 | 102.2 | — | 421.7 |
| 6 b | 200 | 160.2 | 51800 | 120.0 | 1.19 | 67686 | 158 | 1.12 | 107.2 | — | 427.3 |
| 6 c | 100 | 70.4 | 24500 | 54.4 | 1.29 | 29759 | 67 | 1.28 | 14.8 | — | 420.2 |

[1] determined from UV/VIS spectra, chloroform, $\epsilon = 4.96 * 10^4$ l/mol * cm
[2] determined from GPC elugrams, eluent: THF, calibration curve: polystyrene, 30° C.
[3] determined from MALDI-TOF mass spectra
[4] determined from DSC diagram, two heating curves, one cooling curve, −160° C.–300° C., heating rate: 10° C./min
[5] determined from TGA curve, 10° C./min, center point 4.3.2 PS 7 a–b

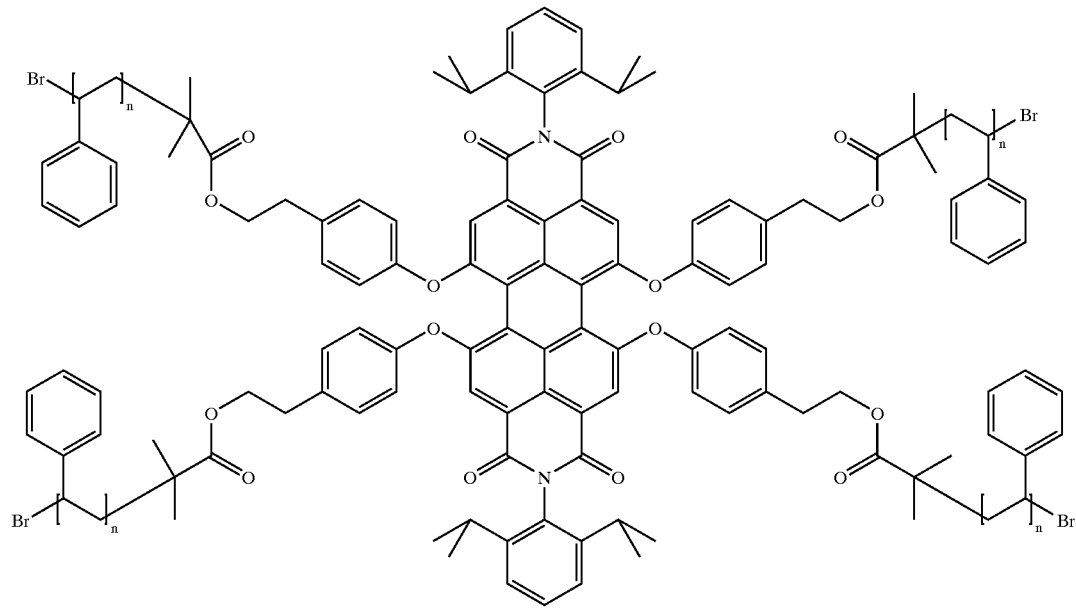

TABLE 13

| No. | Initiator | CuBr | Bpy | Monomer | Solv. | Conversion |
|---|---|---|---|---|---|---|
| 7 a | 300 mg 0.162 mmol | 93.0 mg 0.649 mmol | 0.202 g 1.3 mmol | 6.76 g 64.9 mmol | — | 67% |
| 7 b | 300 mg 0.162 mmol | 93.0 mg 0.648 mmol | 0.202 g 1.3 mmol | 3.38 g 32.45 mmol | — | 60% |

Characterization:

TABLE 14

Characterization and thermal properties of the PCL 4-arm stars produced

| No. | DP target | $DP^1$ | $M_n^2$ | $DP^2$ | $M_w/M_n^2$ | $M_n^3$ | $DP^3$ | $M_w/M_n^3$ | $T_g$ (°C.)[4] | m.p. (°C.)[4] | d.p. (°C.)[5] |
|---|---|---|---|---|---|---|---|---|---|---|---|
| 7 a | 100 | 67.1 | 23670 | 52.4 | 1.24 | 18095 | 39 | 1.2 | 103.3 | — | 410.5 |
| 7 b | 50 | 29.9 | 11390 | 22.9 | 1.27 | 8513 | 16 | 1.2 | 104.2 | — | 411.6 |

[1] determined from UV-VIS spectra, chloroform, $\epsilon = 4.96 * 10^4$ l/mol * cm
[2] determined from GPC elugrams, eluent: THF, calibration curve: polystyrene, 30° C.
[3] determined from MALDI-TOF mass spectra
[4] determined from DSC diagram, two heating curves, one cooling curve, −160° C.–300° C., heating rate: 10° C./min
[5] determined from TGA curve, 10° C./min, center point

Example 2

Preparation of Star-shaped Fluorescent Polypeptides

1. Polymerization Experiments

A solution of the corresponding α-amino acid N-carboxyanhydride in dry DMF (about 0.2 g/ml) was introduced into a Schlenk flask provided with a drying tube. The α-amino acid N-carboxyanhydrides γ-benzyl-L-glutamate N-carboxyanhydride (Bn-Glu NCA) and ε-benzyloxycarbonyl-L-lysine N-carboxyanhydride (Z-Lys NCA) used were synthesized by the procedure described by Poche et al., Syn. Commun. 29 (1999), 843. A solution of the above-obtained compound N,N'-bis(2,6-diisopropylphenyl)-1,6,7,12-tetra[4-(2-aminoethyl)phenoxy]perylene-3,4,9,10-tetracarboxylic acid diimide in dry DMF was then added to the Schlenk flask, and the reaction mixture was stirred at room temperature. The amount of initiator solution depended on the desired arm length of the star polymer, which was controlled via the molar ratio of α-amino acid N-carboxyanhydride and initiator N,N'-bis-(2,6-diisopropylphenyl)-1,6,7,12-tetra[4-(2-aminoethyl)phenoxy]perylene-3,4,9,10-tetracarboxylic acid diimide. After 5 days, the solution was slowly added to a 20-fold (vol/vol) excess of diethyl ether. The precipitated polymer was filtered off and vacuum-dried.

Poly(γ-benzyl-L-glutamate) star polymer (I):

$^1$H-NMR (500 MHz, $C_2D_2Cl_4$): δ=8.23 (s, 4H; perylene), 7.25 (b, 6H+5H×n; Ph-H+Bn-H), 7.02 (b, 8H; Ph-H), 6.89 (b, 8H; Ph-H), 5.0 (s, 2H×4n; Bn-$CH_2$—), 4.0 (b, 1H×4n; $C_α$—H), 2.30 (b, 4H×n; —$CH_2CH_2$—), 1.05 (b, 24H; —$CH_{3\ isopropyl}$)

Poly(ε-benzyloxycarbonyl-L-lysine) star polymer (II):

$^1$H-NMR (500 MHz, $C_2D_2Cl_4$): δ=7.25 (b, 5H×4n; Bn-H), 5.0 (b, 2H×4n; Bn-$CH_2$—), 3.90 (b, 1H×4n; $C_α$—H), 3.10 (b, 2H×4n; —$CH_2NH$—), 2.0 (b, 2H×4n; —$CH_2$—), 1.50 (b, 4H×4n; —$CH_2CH_2$—), 1.05 (b, 24H, $CH_{3\ isopropyl}$)

n indicates the average number of monomer units per arm.

2. Removal of the Protecting Groups from poly(γ-benzyl-L-glutamate) star polymer (I) and from poly(ε-benzyloxycarbonyl-L-lysine) star polymer (II)

A four-fold molar excess of HBr (33% by weight in ACOH) was added to a solution of compound I or compound II in trifluoroacetic acid. The reaction mixture was stirred at room temperature for 1 hour. Diethyl ether was then added, and the precipitated polymer was washed copiously with diethyl ether. After drying under reduced pressure, the poly(L-glutamic acid) star polymer (III) and the poly(L-lysine) star polymer (IV) were obtained in quantitative yield.

Poly(L-glutamic acid) star polymer (III):

$^1$H-NMR (300 MHz, $D_2O$): δ=8.30 (b, 4H; perylene), 7.30 (b, 6H; Ph-H), 7.13 (b, 8H; Ph-H), 6.94 (b, 8H; Ph-H), 4.00 (b, 1H×4n; $C_α$—H), 2.20 (b, 1H×4n; —$CH_2CH_2$—), 1.03 (b, 24H; —$CH_{3\ isopropyl}$)

Poly(L-lysine) star polymer (IV):

$^1$H-NMR (300 MHz, $D_2O$): δ=8.23 (b, 4H; perylene), 7.45 (b, 6H; Ph-H), 7.15 (b, 8H; Ph-H), 7.04 (b, 8H; Ph-H), 4.30 (t, $C_α$—H; 1H×4n), 3.00 (t, —$CH_2$—NH—R; 2H×4n), 1.70 (b, 4H×4n; —$CH_2CH_2$—), 1.40 (b, 2H×4n, —$CHCH_2$—), 1.10 (b, 24H; —$CH_{3\ isopropyl}$)

We claim:

1. A method of forming a polymer comprising:
   adding a perylene-3,4,9,10-tetracarboxylic acid diimide compound of formula (I) to a polymerization reaction:

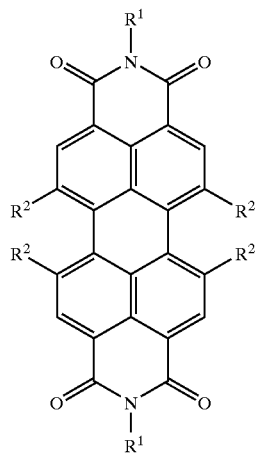

(I)

wherein, each $R^1$ is independently an alkyl or aryl group, which may be unbranched or branched, unsubstituted or substituted, and may optionally contain at least one substituent functional group Y, each $R^2$ is independently H, $C_1$–$C_4$-alkyl, $C_1$–$C_4$-alkoxy, $C_5$–$C_{15}$-aryl, $C_5$–$C_{15}$-aryloxy or a radical which contains at least one substituent functional group Y, wherein Y is selected from the group consisting of hydroxyl, ether, ester, halogen when said radical is not an aryloxy radical, amine, amide, thiol, an ethylenically unsaturated double bond, an acetylenically unsaturated triple bond and carboxyl, which may optionally have a protecting group or an activating group, and said radical is selected from the group consisting of $C_1$–$C_{30}$alkyl radicals, $C_1$–$C_{30}$alkoxy radicals, $C_1$–$C_{30}$alkylthio radicals, $C_5$–$C_{30}$aryl radicals, $C_5$–$C_{30}$aryloxy radicals, $C_5$–$C_{30}$arylthio radicals, $C_1$–$C_{30}$hydrocarbon radicals, silyl radicals and mixtures thereof, wherein at least one $R^2$ contains said functional group Y that enables covalent bonding of said perylene-3,4,9,10-tetracarboxylic acid diimide compound of formula (I) into polymers formed during said polymerization reaction.

2. The method as claimed in claim 1, wherein the perylene-3,4,9,10-tetracarboxylic acid diimide compound of formula (I) has a fluorescence at an emission wavelength of >500 nm.

3. The method as claimed in claim 1, wherein the perylene-3,4,9,10-tetracarboxylic acid diimide compound contains at least one further functional group Y in the radical $R^1$.

4. The method as claimed in claim 1, wherein Y is a primary amino group which optionally has a protecting group.

5. The method as claimed in claim 1, wherein $R^2$ is a radical

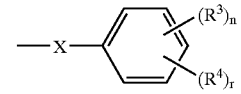

wherein,

X is O or S, $R^3$ is a radical which contains at least one functional group Y, $R^4$ is $C_1$–$C_4$-alkyl, n is an integer from 1 to 5, and r is an integer from 0 to 5, and wherein n+r≤5.

6. The method as claimed in claim 5, wherein $R^2$ is a radical:

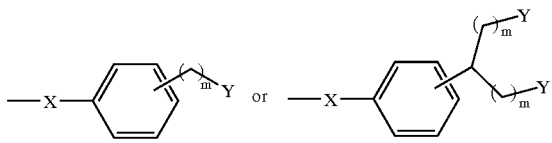

where m is an integer from 1 to 30.

7. The method as claimed in claim 1, wherein the radicals $R^2$ contain at least two functional groups Y.

8. The method as claimed in claim 1, wherein the radicals $R^2$ contain at least four functional groups Y.

9. The method as claimed in claim 1, wherein at least one of the radicals $R^1$ contains an aromatic group.

10. The method as claimed in claim 9, wherein $R^1$ is a radical:

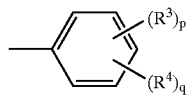

where $R^3$ is a radical which contains at least one substituent functional group Y selected from the group consisting of hydroxyl, ether, ester, halogen, amine, amide, thiol, an ethylenically unsaturated double bond, an acetylenically unsaturated triple bond and carboxyl, which may optionally have a protecting group or an activating group, $R^4$ is $C_1$–$C_4$-alkyl, and p and q are each an integer from 0 to 5, wherein $p+q \leq 5$.

11. The method as claimed in claim 10, wherein $R^1$ is a radical:

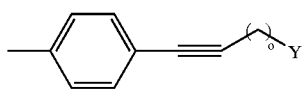

where o is an integer from 1 to 30.

12. A polymer obtained by the reacting at least one monomer with a perylene-3,4,9,10-tetracarboxylic acid diimide compound of formula (I):

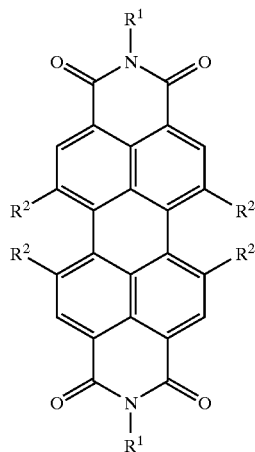

wherein, each $R^1$ is independently an alkyl or aryl group, which may be unbranched or branched, unsubstituted or substituted, and may optionally contain at least one substituent functional group Y, each $R^2$ is independently H, $C_1$–$C_4$-alkyl, $C_1$–$C_4$-alkoxy, $C_5$–$C_{15}$-aryl, $C_5$–$C_{15}$-aryloxy or a radical which contains at least one substituent functional group Y, wherein Y is selected from the group consisting of hydroxyl, ether, ester, halogen when said radical is not an aryloxy radical, amine, amide, thiol, an ethylenically unsaturated double bond, an acetylenically unsaturated triple bond and carboxyl, which may optionally have a protecting group or an activating group, and said radical is selected from the group consisting of $C_1$–$C_{30}$alkyl radicals, $C_1$–$C_{30}$alkoxy radicals, $C_1$–$C_{30}$alkylthio radicals, $C_5$–$C_{30}$aryl radicals, $C_5$–$C_{30}$aryloxy radicals, $C_5$–$C_{30}$arylthio radicals, $C_1$–$C_{30}$ hydrocarbon radicals, silyl radicals and mixtures thereof, wherein at least one $R^2$ contains said functional group Y, and wherein the perylene-3,4,9,10-tetracarboxylic acid diimide compound is covalently bonded to the polymer.

13. The polymer as claimed in claim 12, which is an engineering plastic.

14. The polymer as claimed in claim 12, which is polystyrene, polymethacrylate, polyacrylate, silicone or a combination thereof.

15. The polymer as claimed in claim 12, which is an aliphatic polyester.

16. The polymer as claimed in claim 12, wherein the polymer comprises one or more water-soluble polymer chains.

17. The polymer as claimed in claim 16, wherein the water-soluble polymer chains are selected from the group consisting of polypeptide and polyalkylene oxides.

18. A perylene-3,4,9,10-tetracarboxylic acid diimide compound of formula (I):

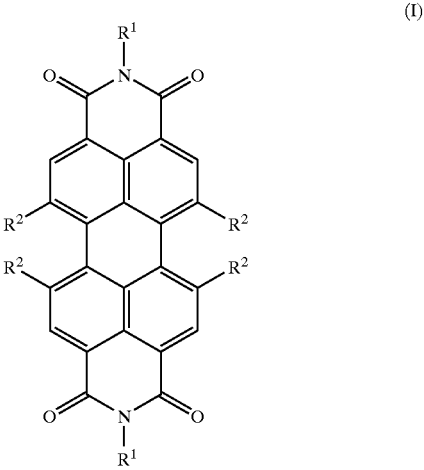

wherein $R^1$ is a radical which contains at least one aromatic ring, each $R^2$ is independently H, halogen, $C_1$–$C_4$-alkyl, $C_1$–$C_4$-alkoxy, $C_5$–$C_{15}$-aryl, $C_5$–$C_{15}$-aryloxy or a radical which contains at least one substituent functional group Y wherein Y is selected from the group consisting of hydroxyl, ether, ester, amine, amide; thiol, an ethylenically unsaturated double bond, an acetylenically unsaturated triple bond and carboxyl, which may optionally have a protecting group or an activating group, and wherein said radical is selected from the group consisting of $C_1$–$C_{30}$alkyl radicals, $C_1$–$C_{30}$alkoxy radicals, $C_1$–$C_{30}$alkylthio radicals, $C_5$–$C_{30}$aryl radicals, $C_5$–$C_{30}$aryloxy radicals, $C_5$–$C_{30}$arylthio radicals, $C_1$–$C_{30}$hydrocarbon radicals, silyl radicals and mixtures thereof, and wherein at least three said functional groups Y are present in the compound and at least three $R^2$ groups contain at least one said substituent functional group Y.

19. A perylene-3,4,9,10-tetracarboxylic acid diimide compound of formula (I)

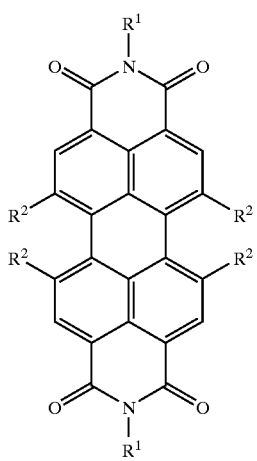

(I)

wherein, each $R^1$ is, independently of the others, an alkyl or aryl group, which may be unbranched or branched, unsubstituted or substituted, at least one $R^1$ contains a halogen, each $R^2$ is independently H, halogen, $C_1$–$C_4$-alkyl, $C_1$–$C_4$alkoxy, $C_5$–$C_{15}$-aryl, $C_5$–$C_{15}$-aryloxy or a radical which contains at least one substituent functional group Y wherein Y is selected from the group consisting of hydroxy, ether, ester, halogen, amine, amide, thiol, an ethylenically unsaturated double bond, an acetylenically unsaturated triple bond and carboxyl, which may optionally have a protecting group or an activating group, wherein said radical is selected from the group consisting of $C_1$–$C_{30}$alkyl radicals, $C_1$–$C_{30}$alkoxy radicals, $C_1$–$C_{30}$alkylthio radicals, $C_5$–$C_{30}$aryl radicals, $C_5$–$C_{30}$aryloxy radicals, $C_5$–$C_{30}$arylthio radicals, $C_1$–$C_{30}$hydrocarbon radicals, silyl radicals and mixtures thereof, and wherein at least one $R^2$ contains said functional group Y.

20. The method of claim 1, wherein the diimide compound is added before polymerization begins.

21. The method of claim 1, wherein the diimide compound is added while polymerization is occurring.

22. The method of claim 1, further comprising forming a polymer covalently bonded to the diimide compound.

23. The method of claim 1, wherein the polymerization reaction is selected from the group consisting of a free-radical polymerization, a ring-opening polymerization of an aliphatic polyester, a ring-opening polymerization of a cyclic siloxane, a ring opening polymerization of an N-carboxy anhydride and a polycondensation reaction.

24. The polymer of claim 12, wherein the polymer is colored.

25. The polymer of claim 12, wherein the polymer is fluorescent.

26. The polymer as claimed in claim 12, wherein the polymer is a polylactide, polycaprolactone, polypeptide or a combination thereof.

27. A product comprising the polymer as claimed in claim 12.

28. A product as claimed in claim 27, selected from the group consisting of a fluorescent solar collector, a laser dye, a green house sheeting, an optoelectronic device, an optical device, a fluorescent label and a fluorescent probe.

29. The diimide compound as claimed in claim 19, wherein $R^1$ contains Br.

30. The method as claimed in claim 1, wherein the perylene-3,4,9,10-tetracarboxylic acid diimide compound is an initiator, a coreactant or a combination thereof.

31. A perylene-3,4,9,10-tetracarboxylic acid diimide compound of formula (I):

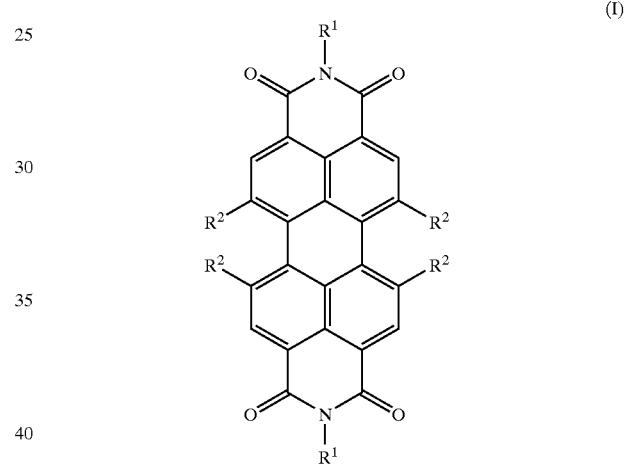

(I)

wherein $R^1$ is a radical which contains at least one aromatic ring, each $R^2$ is independently H, halogen, $C_1$–$C_4$-alkyl, $C_1$–$C_4$-alkoxy, $C_5$–$C_{15}$-aryl, $C_5$–$C_{15}$-aryloxy or a radical which contains at least one substituent functional group Y wherein Y is selected from the group consisting of hydroxyl, ether, ester, amine, amide, thiol, an ethylenically unsaturated double bond, an acetylenically unsaturated triple bond and carboxyl, which may optionally have a protecting group or an activating group, and wherein said radical is selected from the group consisting of $C_1$–$C_{30}$alkyl radicals, $C_1$–$C_{30}$alkoxy radicals, $C_1$–$C_{30}$alkylthio radicals, $C_5$–$C_{30}$aryl radicals, $C_5$–$C_{30}$aryloxy radicals, $C_5$–$C_{30}$arylthio radicals, $C_1$–$C_{30}$saturated hydrocarbon radicals, silyl radicals and mixtures thereof, and wherein at least three said functional groups Y are present in the compound.

* * * * *